(12) United States Patent
Jander et al.

(10) Patent No.: US 9,879,273 B2
(45) Date of Patent: Jan. 30, 2018

(54) COMPOSITIONS AND METHODS FOR INCREASING METHIONINE CONTENT IN PLANTS

(71) Applicant: Boyce Thompson Institute for Plant Research, Ithaca, NY (US)

(72) Inventors: Georg Jander, Ithaca, NY (US); Tengfang Huang, Ithaca, NY (US); Vijay Joshi, Ithaca, NY (US)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 55 days.

(21) Appl. No.: 14/657,724

(22) Filed: Mar. 13, 2015

(65) Prior Publication Data
US 2016/0017354 A1    Jan. 21, 2016

Related U.S. Application Data

(60) Provisional application No. 61/953,727, filed on Mar. 14, 2014.

(51) Int. Cl.
*C12N 15/82*    (2006.01)
(52) U.S. Cl.
CPC ..... *C12N 15/8253* (2013.01); *C12N 15/8218* (2013.01)

(58) Field of Classification Search
None
See application file for complete search history.

(56) References Cited

U.S. PATENT DOCUMENTS

| 3,619,211 A | 11/1971 | Chang et al. |
| 2010/0199386 A1* | 8/2010 | Bhaskar .............. C12N 15/8218 800/284 |

OTHER PUBLICATIONS

Goyer et al, 2007, Plant Cell Physiology, 48:232-242.*
Dancs et al, 2008, BMC Plant Biology, 8:1-10.*
Rensink et al, 2005, Genome, 48:598-605.*
Muth et al, 2008, Plant Biotechnology Journal, 6:576-584.*
Amir, Rachel et al., "Cystathionine γ-synthasse and threonine synthase operate in concert to regulate carbon flow towards methionine in plants", TRENDS in Plant Science, 7(4): 153-156 (2002).
Bartlem, Derek et al., "Mutation in the Threonine Synthase Gene Results in an Over-Accumulation of Soluble Methionine in *Arabidopsis*", Plant Physiology, 123: 101-110 (2000).
Bombarely, Aureliano et al., "The Sol Genomics Network (solgenomics.net): growing tomatoes using Perl", Nucleic Acids Research, 39: D1149-D1155 (2011).
Bourgis, Fabienne et al., "S-Methylmethionine Plays a Major Role in Phloem Sulfur Transport and Is Synthesized by a Novel Type of Methyltransferase", The Plant Cell, 11: 1485-1497 (1999).
Chiba, Yukako et al., "Evidence for Autoregulation of Cystathionine γ-Synthase mRNA Stability in *Arabidopsis*", Science, 286: 1371-1374 (1999).
Cohen, Steven A. et al., "Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography", Analytical Biochemistry, 211: 279-287 (1993).
Curien, Gilles et al., "Allosteric Activation of *Arabidopsis* Threonine Synthase by S-Adenosylmethionine", Biochemistry, 37: 13212-13221 (1998).
Dancs, Gabor et al., "The effects of enhanced methionine synthesis on amino acid and anthocyanin content of potato tubers", BMC Plant Biology, 8: 65 (2008).
Di, Rong et al., "Enhancement of the Primary Flavor Compound Methional in Potato by Increasing the Level of Soluble Methionine", J. Agric. Food Chem., 51: 5695-5702 (2003).
Goyer, Aymeric et al., "Functional Characterization of a Methionine γ-Lyase in *Arabidopsis* and its Implication in an Alternative to the Reverse Trans-sulfuration Pathway", Plant Cell Physiol., 48(2): 232-242 (2007).
Helliwell, Chris et al., "Constructs and methods for high-throughput gene silencing in plants", Methods, 30: 289-295 (2003).
Hesse, Holger et al., "Current understanding of the regulation of methionine biosynthesis in plants", Journal of Expenmental Botany, 55(404): 1799-1808 (2004).
Houmard, Nancy M. et al., "High-lysine corn generated by endosperm-specific suppression of lysine catabolism using RNAi", Plant Biotechnology Journal, 5: 605-614 (2007).
Huang, Shihshieh et al., "High-lysine corn produced by the combination of enhanced lysine biosynthesis and reduced zein accumulation", Plant Biotechnology Journal, 3: 555-569 (2005).
Jander, Georg et al., "Recent Progress in Deciphering the Biosynthesis of Aspartate-Derived Amino Acids in Plants", Molecular Plant, 3(1): 54-65 (2010).
Joshi, Vijay et al., "*Arabidopsis* Methionine γ-Lyase Is Regulated According to Isoleucine Biosynthesis Needs But Plays a Subordinate Role to Threonine Deaminase", Plant Physiology, 151: 367-378 (2009).
Karchi, Nagai et al., "Lysine synthesis and catabolism are coordinately regulated during tobacco seed development", Proc. Natl. Acad. Sci. USA, 91: 2577-2581 (1994).
Kim, Jungsup et al., "Constitutive Overexpression of Cystathionine γ-Synthase in *Arabidopsis* Leads to Accumulation of Soluble Methionine and S-Methylmethionine", Plant Physiology, 128: 95-107 (2002).
Koch, Wolfgang et al., "Reduced amino acid content in transgenic potato tubers due to antisense inhibition of the leaf H+/amino acid symporter StAAP1", The Plant Journal, 33: 211-220 (2003).
Kreft, Oliver et al., Functional Analysis of Cystathionine γ-Synthase in Genetically Engineered Potato Plants, Plant Physiology, 131: 1843-1854 (2003).
Kumar, G. N. Mohan et al., "Extraction of RNA from Fresh, Frozen, and Lyophiolized Tuber and Root Tissues", J. Agric. Food Chem., 55: 1674-1678 (2007).
Less, Hadar et al., "Principal Transcriptional Programs Regulating Plant Amino Acid Metabolism in Response to Abiotic Stresses", Plant Physiology, 147: 316-330 (2008).

(Continued)

*Primary Examiner* — Jason Deveau Rosen
(74) *Attorney, Agent, or Firm* — Kathleen D. Rigaut; Dann, Dorfman, Herrell and Skillman, P.C.

(57) ABSTRACT

Compositions and methods are provided for increasing methionine content in plants are disclosed.

8 Claims, 24 Drawing Sheets

(56) References Cited

OTHER PUBLICATIONS

Mourad, George et al., "L-O-Methylthreonine-Resistant Mutant of *Arabidopsis* Defective in Isoleucine Feedback Regulation", Plant Physiol., 107: 43-52 (1995).
Nguyen, Huu Cuong et al., "Improving the nutritive value of rice seeds: elevation of cysteine and methionine contents in rice plants by ectopic expression of a bacterial serine acetyltransferase", Journal of Experimental Botany, 63(16): 5991-6001 (2012).
Nicot, Nathalie et al., "Housekeeping gene selection for real-time RT-PCR normalization in potato during biotic and abiotic stress", Journal of Experimental Botany, 56(421): 2907-2914 (2005).
Onouchi, Hitoshi et al., "Nascent peptide-mediated translation elongation arrest coupled with mRNA degradation in the CGS1 gene of *Arabidopsis*", Genes & Development, 19: 1799-1810 (2005).
Perl, Avihai et al., "Regulation of lysine synthesis in transgenic potato plants expressing a bacterial dihydrodipicolinate synthase in their chloroplasts", Plant Molecular Biology, 19: 815-823 (1992).
Rebeille, Fabrice et al., "Methionine catabolism in *Arabidopsis* cells is initiated by a cleave process and leads to S-methylcysteine and isoleucine syntheses", PNAS, 103(42): 15687-15692 (2006).
Reyes, Allan R. et al., "Genetic manipulation of lysine catabolism in maize kernels", Plant Mol. Biol., 69: 81-89 (2009).
Rinder, J. et al., "Regulation of aspartate-derived amino acid homoestasis in potato plants (*Solanum tuberosum* L.) by expression of *E. coli* homoserine kinase", Amino Acids, 34: 213-222 (2008).
Rommens, Caius M. et al., "Tastier and Healthier Alternatives to French Fries", Journal of Food Science, 75:(4): H109-H115 (2010).
Shaul, Orit et al., "Increased lysine synthesis in tobacco plants that express high levels of bacterial dihydrodipicolinate synthase in their chloroplasts", The Plant Journal, 2(2): 203-209 (1992).
Shen, Bo et al., "High free-methionine and decreased lignin content result from a mutation in the *Arabidopsis* S-adenosyl-L-methionine synthetase 3 gene", The Plant Journal, 29(3): 371-380 (2002).
Stepansky, A. et al., "Lysine catabolism, an effective versatile regulator of lysine level in plants", Amino Acids, 30: 121-125 (2006).
Tang, Guilliang et al., "Regulation of Lysine Catabolism through Lysine-Ketoglutarate Reductase and Saccharopine Dehydrogenase in *Arabidopsis*", The Plant Cell, 9: 1305-1316 (1997).
Van Eck, J. et al., "Enhancing Beta-Carotene Content in Potato by RNAi-mediated Silencing of the Beta-Carotene Hydroxylase Gene", Amer. J. of Potato Res., 84: 331-342 (2007).
Wesley, S. Varsha et al., "Construct design for efficient, effective and high-throughput gene silencing in plants", The Plant Journal, 27(6): 581-590 (2001).
Xu, Xun et al., Nature, "Genome sequence and analysis of the tuber crop potato", Nature, 475: 189-195 2011.
Zeh, Michaela et al., "Antisense Inhibition of Threonine Synthase Leads to High Methionine Content in Transgenic Potato Plants", Plant Physiol., 127: 792-802 (2001).
Zhu, Xiaohong et al., "Increased Lysine Synthesis Coupled with a Knockout of Its Catabolism Synergistically Boosts Lysine Content and Also Transregulates the Metabolism of Other Amino Acids in *Arabidopsis* Seeds", The Plant Cell, 15: 845-853 (2003).
Lindsay, R.C., "Flavors", Food Chemistry, Owen R. Fennema ed., New York, Marchel Dekker, Inc. (1996).

\* cited by examiner

Figure 11 atgaattcggcgaacacggcggcgttaacatgtccatcgaggcctccgccaccttcaccgtcatggaaccggagacgatgcgccgcatgtt
cgccggagaacttggtcctgaccgtgatttcttcatctacagccgtcatttcaatccgacggtgctcaatctcggtcgcctcatggctgcgcttg
agggaacggaagctgcttactgtacggcttccggcatgtcggcgatatcatcggtgatgttacagctctgcagttcaggtggacacgtggtg
gcttcgcagacgttgtatggtgggacccatgcgttgctcacgcattttttaccgagggcttgtaacataacgacgtcgtttgtggatgtaaggg
atttggaaatggttaaggaagctatagttgaagggagaacaaatgtgctgtatttgagtcagtgtcaaatccgacgctgacggtggctaacat
cccggagttgagcaggatagcgcatgaaaaaggtgtgacagtggtggtggacaacacttttgctccgatggtgctatcgccggtgaaaatg
ggggctgatgttgttgttcatagtatttccaagtacattagcggtgcagctga

SEQUENCE LISTING

<160> NUMBER OF SEQ ID NOS: 14

<210> SEQ ID NO 1
<211> LENGTH: 610
<212> TYPE: DNA
<213> ORGANISM: Artificial Sequence
<220> FEATURE:
<223> OTHER INFORMATION: RNAi

<400> SEQUENCE: 1

| | | | | | |
|---|---|---|---|---|---|
| atgaattcgg | cgaacacggc | ggcgttaaca | tgtccatcga | ggcctccgcc | accttcaccg | 60 |
| tcatggaacc | ggagacgatg | cgccgcatgt | tcgccggaga | acttggtcct | gaccgtgatt | 120 |
| tcttcatcta | cagccgtcat | ttcaatccga | cggtgctcaa | tctcggtcgc | ctcatggctg | 180 |
| cgcttgaggg | aacggaagct | gcttactgta | cggcttccgg | catgtcggcg | atatcatcgg | 240 |
| tgatgttaca | gctctgcagt | tcaggtggac | acgtggtggc | ttcgcagacg | ttgtatggtg | 300 |
| ggacccatgc | gttgctcacg | cattttttac | cgagggcttg | taacataacg | acgtcgtttg | 360 |
| tggatgtaag | ggatttggaa | atggttaagg | aagctatagt | tgaagggaga | acaaatgtgc | 420 |
| tgtattttga | gtcagtgtca | aatccgacgc | tgacggtggc | taacatcccg | gagttgagca | 480 |
| ggatagcgca | tgaaaaaggt | gtgacagtgg | tggtggacaa | cacttttgct | ccgatggtgc | 540 |
| tatcgccggt | gaaaatgggg | gctgatgttg | ttgttcatag | tatttccaag | tacattagcg | 600 |
| gtgcagctga | | | | | | 610 |

<210> SEQ ID NO 2
<211> LENGTH: 49
<212> TYPE: DNA
<213> ORGANISM: Artificial Sequence
<220> FEATURE:
<223> OTHER INFORMATION: primer

<400> SEQUENCE: 2
ggggacaagt ttgtacaaaa aagcaggctt catgaattcg gcgaacacg        49

<210> SEQ ID NO 3
<211> LENGTH: 50
<212> TYPE: DNA
<213> ORGANISM: Artificial Sequence
<220> FEATURE:
<223> OTHER INFORMATION: primer

<400> SEQUENCE: 3
ggggaccact ttgtacaaga aagctgggtc tcagctgcac cgctaatgta       50

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcaccaatcc aggtgaaatc        20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5

```
gtggtctttc ggtatttaag                                                 20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
tgctgctgta acaagatgg                                                  19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
attttgtcag ggttgtaacc                                                 20

<210> SEQ ID NO 8
<211> LENGTH: 16
<212> TYPE: DNA
<213> ORGANISM: Artificial Sequence
<220> FEATURE:
<223> OTHER INFORMATION: primer

<400> SEQUENCE: 8
tgatatcatt gcaggt                                                     16

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
tgcaagttca aaggccac                                                   18

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
caaatatatt agtggggctg cc                                              22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
atcttagcat tcatggttgg                                                 20

<210> SEQ ID NO 12
<211> LENGTH: 451
<212> TYPE: PRT
```

<213> ORGANISM: Solanum tuberosum

<400> SEQUENCE: 12

```
Met Ala Asp Thr Leu Asn Gln Asn Thr Asn Ile Val Ala Ser Asn Lys
 1               5                  10                  15
Lys Arg Ser Ser Gly Ser Asp Glu Cys Asp His His Asp Asp Ser Phe
            20                  25                  30
Phe Val Ser Lys Lys Gln Ser Lys Ser Leu Val Trp Glu Asp Pro Ala
        35                  40                  45
Ala Ala Leu Ala Asn Ala Arg His Glu Phe Gly Glu His Gly Gly Val
    50                  55                  60
Asn Met Ser Ile Glu Ala Ser Ala Thr Phe Thr Val Met Glu Pro Glu
65                  70                  75                  80
Thr Met Arg Arg Met Phe Ala Gly Glu Leu Gly Pro Asp Arg Asp Phe
                85                  90                  95
Phe Ile Tyr Ser Arg His Phe Asn Pro Thr Val Leu Asn Leu Gly Arg
            100                 105                 110
Leu Met Ala Ala Leu Glu Gly Thr Glu Ala Ala Tyr Cys Thr Ala Ser
        115                 120                 125
Gly Met Ser Ala Ile Ser Ser Val Met Leu Gln Leu Cys Ser Ser Gly
    130                 135                 140
Gly His Val Val Ala Ser Gln Thr Leu Tyr Gly Gly Thr His Ala Leu
145                 150                 155                 160
Leu Thr His Phe Leu Pro Arg Ala Cys Asn Ile Thr Thr Ser Phe Val
                165                 170                 175
Asp Val Arg Asp Leu Glu Met Val Lys Glu Ala Ile Val Glu Gly Arg
            180                 185                 190
Thr Asn Val Leu Tyr Phe Glu Ser Val Ser Asn Pro Thr Leu Thr Val
        195                 200                 205
Ala Asn Ile Pro Glu Leu Ser Arg Ile Ala His Glu Lys Gly Val Thr
    210                 215                 220
Val Val Val Asp Asn Thr Phe Ala Pro Met Val Leu Ser Pro Val Lys
225                 230                 235                 240
Met Gly Ala Asp Val Val His Ser Ile Ser Lys Tyr Ile Ser Gly
                245                 250                 255
Ala Ala Asp Ile Ile Ala Gly Ala Val Cys Gly Pro Ala Ser Leu Val
            260                 265                 270
Asn Ser Met Met Asp Leu His Gln Gly Ser Leu Met Leu Leu Gly Pro
        275                 280                 285
Thr Met Asn Pro Lys Val Ala Phe Glu Leu Ala Glu Arg Leu Pro His
    290                 295                 300
Leu Gly Leu Arg Met Lys Glu His Cys Lys Arg Ala Leu Glu Tyr Ala
305                 310                 315                 320
Ser Arg Met Thr Lys Leu Gly Leu Lys Val Ile Tyr Pro Gly Leu Glu
                325                 330                 335
Asp His Pro Asp His Ala Leu Ile Lys Ser Met Ala Asn Lys Asp Tyr
            340                 345                 350
Gly Tyr Gly Gly Ile Leu Cys Val Asp Met Glu Thr Glu Glu Arg Ala
        355                 360                 365
Asn Arg Leu Met Asn Val Leu Gln Asn Phe Thr Gln Phe Gly Phe Met
    370                 375                 380
Ala Val Ser Leu Gly Tyr Tyr Glu Thr Leu Met Ser Cys Ser Gly Ser
385                 390                 395                 400
```

Ser Thr Ser Ser Glu Leu Asn Asn Glu Glu Lys Glu Leu Ala Gly Ile
            405                 410                 415

Ser Pro Gly Leu Val Arg Met Ser Ile Gly Tyr Asn Gly Ser Leu Glu
            420                 425                 430

Gln Lys Trp Ser Gln Leu Asp Lys Ala Leu Ser Lys Met Gln Glu Lys
            435                 440                 445

Met Pro Phe
    450

<210> SEQ ID NO 13
<211> LENGTH: 433
<212> TYPE: PRT
<213> ORGANISM: Solanum tuberosum

<400> SEQUENCE: 13

Met Ala Gly Lys Ser Glu Gln Asn Ala Val Val Leu Asp Lys Gln Arg
  1               5                  10                  15

Pro Ala Asn Val Ala Gln Lys Ser Met Lys His His Leu Ile Leu Glu
             20                  25                  30

Asp Pro Ala Ala Ala Leu Ala Asn Val Arg His Glu Phe Gly Glu His
         35                  40                  45

Gly Gly Val Asn Met Ser Ile Glu Ala Ser Ile Thr Phe Thr Val Met
     50                  55                  60

Glu Pro Glu Asn Leu Ser Arg Met Phe Ala Gly Glu Leu Gly Pro Asp
 65                  70                  75                  80

Arg Asp Phe Phe Ile Tyr Ser Arg His Leu Asn Pro Thr Val Leu Asn
                 85                  90                  95

Leu Ser Arg Leu Met Ala Ala Leu Glu Gly Thr Glu Ala Ala Tyr Cys
            100                 105                 110

Thr Ser Ser Gly Met Ser Ala Ile Ser Ser Val Leu Leu Gln Leu Cys
            115                 120                 125

Ser Ser Gly Asp His Ile Val Ala Ser Arg Ser Leu Tyr Gly Gly Thr
        130                 135                 140

Tyr Ala Leu Leu Thr His Phe Leu Pro Lys Ala Cys Asn Ile Thr Thr
145                 150                 155                 160

Ser Phe Val Asp Ile Arg Asp Leu Asn Met Val Glu Glu Ala Ile Val
                165                 170                 175

Glu Gly Arg Thr Lys Val Leu Tyr Phe Glu Ser Ile Ser Asn Pro Thr
            180                 185                 190

Leu Met Val Thr Asp Ile Pro Ala Leu Cys Arg Ile Ala His Ser Lys
        195                 200                 205

Gly Val Phe Val Val Val Asp Asn Thr Phe Ala Pro Met Val Leu Ser
210                 215                 220

Pro Ala Arg Leu Gly Ala Asp Val Val Val His Ser Ile Ser Lys Tyr
225                 230                 235                 240

Ile Ser Gly Ala Ala Asp Val Ile Ala Gly Ala Val Cys Gly Pro Ala
                245                 250                 255

Ser Leu Ile Asn Ser Met Met Asp Leu Arg Glu Gly Ser Leu Met Leu
            260                 265                 270

Leu Gly Pro Thr Met Asn Ala Lys Ile Ala Phe Glu Leu Ser Glu Arg
        275                 280                 285

Leu Pro His Leu Gly Leu Arg Met Lys Glu His Ser Asn Arg Ala Leu
    290                 295                 300

Val Phe Ala Thr Arg Ile Thr Lys Leu Gly Leu Lys Val Ile Tyr Pro
305                 310                 315                 320

```
Gly Leu Glu Asn His Pro Asp His Gly Leu Leu Lys Ser Leu Ala Asn
                325                 330                 335

Glu Asp Tyr Gly Tyr Gly Gly Ile Leu Cys Val Asp Met Glu Thr Glu
            340                 345                 350

Glu Lys Ala Asn Cys Leu Met Asn Val Leu Gln Asn Cys Thr Gln Phe
        355                 360                 365

Gly Leu Ile Ala Val Ser Leu Gly Tyr Tyr Glu Thr Leu Met Ser Cys
    370                 375                 380

Ser Gly Asn Ser Thr Ser Ser Glu Met Asn Asn Gln Glu Lys Glu Leu
385                 390                 395                 400

Ala Gly Ile Ser Pro Gly Leu Val Arg Met Ser Ile Gly Tyr Asn Gly
                405                 410                 415

Thr Leu Glu Gln Lys Trp Ser Gln Leu Glu Lys Ala Leu Ser Gln Met
            420                 425                 430

Gln

<210> SEQ ID NO 14
<211> LENGTH: 441
<212> TYPE: PRT
<213> ORGANISM: Arabidopsis thaliana

<400> SEQUENCE: 14

Met Ala His Phe Leu Glu Thr Gln Glu Pro Leu Val Phe Ser Gly Lys
  1               5                  10                  15

Lys Arg Asn Asp Arg Asp Asp Glu Asp Gly Asp Ala Leu Val Ala Lys
             20                  25                  30

Lys Ser Ala Leu Ala Val Cys Asp Ala Asp Pro Ala Ala Ala Ile Ala
         35                  40                  45

Asn Ile Arg His Glu Phe Glu His Gly Gly Val Asn Met Ser Ile
     50                  55                  60

Glu Ala Ser Ala Thr Phe Thr Val Met Glu Pro Asp Thr Met Arg Arg
 65                  70                  75                  80

Met Phe Thr Gly Glu Leu Gly Pro Asp Asn Asp Phe Tyr Val Tyr Ser
                 85                  90                  95

Arg His Phe Asn Pro Thr Val Leu Asn Leu Ser Arg Gln Met Ala Ala
            100                 105                 110

Leu Glu Gly Thr Gln Ala Ala Tyr Cys Thr Ser Ser Gly Met Ser Ala
        115                 120                 125

Ile Ser Ser Val Met Leu Gln Leu Cys Ser Ser Gly Gly His Val Val
    130                 135                 140

Ala Ala Ser Thr Leu Tyr Gly Gly Thr His Ala Leu Leu Ser His Phe
145                 150                 155                 160

Leu Pro Arg Thr Cys Asn Ile Thr Thr Ser Phe Val Asp Ile Thr Asp
                165                 170                 175

His Gly Ala Val Ala Asn Ala Ile Val Glu Gly Arg Thr Gln Val Leu
            180                 185                 190

Tyr Phe Glu Ser Val Ala Asn Pro Thr Leu Thr Val Ala Asp Ile Pro
        195                 200                 205

Glu Leu Ser Arg Met Ala His Glu Lys Gly Val Thr Val Val Val Asp
    210                 215                 220

Asn Thr Phe Ala Pro Met Val Leu Ser Pro Ala Lys Leu Gly Ala Asp
225                 230                 235                 240

Val Val Val His Ser Ile Ser Lys Phe Ile Ser Gly Gly Ala Asp Ile
                245                 250                 255
```

```
Ile Ala Gly Ala Val Cys Gly Ser Glu Asn Leu Val Lys Glu Met Met
            260                 265                 270

Asp Leu Arg Gly Gly Ser Leu Met Leu Leu Gly Pro Thr Met Asn Ala
        275                 280                 285

Lys Val Ala Phe Glu Leu Ser Glu Arg Ile Pro His Leu Gly Leu Arg
        290                 295                 300

Met Arg Glu His Ser His Arg Ala Gln Val Tyr Ala Glu Arg Met Arg
305                 310                 315                 320

Asp Leu Gly Met Lys Val Ile Tyr Pro Gly Leu Glu Thr His Pro Gln
                325                 330                 335

His Lys Leu Phe Lys Gly Met Val Asn Arg Asp Tyr Gly Tyr Gly Gly
            340                 345                 350

Leu Leu Ser Ile Asp Met Glu Thr Glu Glu Lys Ala Asn Lys Leu Met
            355                 360                 365

Ala Tyr Leu Gln Asn Ala Thr Gln Phe Gly Phe Met Ala Val Ser Leu
        370                 375                 380

Gly Tyr Tyr Glu Thr Leu Met Ser Cys Ser Gly Ser Ser Thr Ser Ser
385                 390                 395                 400

Glu Leu Asp Pro Ser Gln Lys Glu Ala Ala Gly Ile Ser Pro Gly Leu
            405                 410                 415

Val Arg Met Ser Val Gly Tyr Val Gly Thr Leu Glu Gln Lys Trp Thr
            420                 425                 430

Gln Phe Glu Lys Ala Phe Leu Arg Met
            435                 440
```

COMPOSITIONS AND METHODS FOR INCREASING METHIONINE CONTENT IN PLANTS

This application claims priority to U.S. Provisional Application No. 61/953,727 filed Mar. 14, 2014, the entire disclosure being incorporated herein by reference.

This invention was made with government support under Grant Number MCB-1022017 awarded by the National Science Foundation. The government has certain rights in the invention.

FIELD OF THE INVENTION

This invention relates the fields of transgenic plants having improved traits. More specifically, the invention provides materials and methods suitable for increasing methionine content in targeted plants species, particularly in potatoes.

BACKGROUND OF THE INVENTION

Several publications and patent documents are cited throughout the specification in order to describe the state of the art to which this invention pertains. Each of these citations is incorporated herein by reference as though set forth in full.

The potato (*Solanum tuberosum*), one of the world's most important food crops, produces more dry matter and protein per hectare than the major cereals (FAOSTAT 2010; http://faostat.fao.org). In addition to direct human consumption, a large portion of the potato crop is used as animal feed, where it serves as an important source of dietary amino acids. Free amino acids account for about 50% of the total nitrogen found in potato tubers (Koch et al., 2003). However, the essential amino acid methionine (Met) is limiting when compared to the daily uptake value recommended by the World Health Organization (Woolfe et al., 1987). Thus, increasing Met levels can augment the nutritional value of potato tubers. In addition, Met is the precursor of methional, a volatile compound produced under high temperature that is the major component of the attractive aroma associated with baked potatoes, potato chips, and French fries (Lindsay, 1996). Although the taste of potato chips can be improved by free Met supplementation before frying (Chang and Reddy, 1971), the cost is considered prohibitive. Therefore, due to the associated nutritional and aroma benefits, increasing the tuber Met content is of interest to the potato industry.

SUMMARY OF THE INVENTION

In accordance with the present invention, methionine gamma lyase (MGL) has been identified as a key modulator of methionine production in plants, particularly in potatoes. Decreasing production of MGL results in increased methionine production as discussed in detail hereinbelow. Thus, in one aspect of the invention, inhibitors of MGL expression are provided. In one aspect, a vector comprising an RNAi effective to down modulate expression of methionine gamma lyase in a target plant, thereby increasing methionine content in plant cells expressing said RNAi is provided. In a particularly preferred embodiment, the RNAi has the sequence of SEQ ID NO: 1. In another embodiment of the invention, the RNAi is operably linked to at least one regulatory sequence.

In yet another aspect of the invention, a method for producing a plant which exhibits enhanced methionine content is provided. An exemplary method comprises transforming a plant cell with the MGL inhibitor, such as the RNAi described above, and regenerating a plant from the transformed plant cell. Also provided is a plant cell, plant part, or seed comprising an inhibitor of MGL.

In a particularly preferred embodiment, the invention provides a compositions and methods for increasing methionine content in potatoes. An exemplary method entails transforming potato plant cells with a MGL inhibitor and growing fertile mature plants from the transformed plant cells obtained therefrom under conditions suitable to obtain potatoes; and harvesting potatoes containing increased levels of methionine compared to potatoes obtained from plants lacking the MGL inhibitor. In one embodiment, the MGL inhibitor is an RNAi directed against MGL encoding nucleic acids.

BRIEF DESCRIPTION OF THE DRAWINGS

(FIG. 3a) Normal and abnormal leaves from plants at tuber harvest. Wildtype and empty vector controls (EV5, EV8) and most MGL silencing lines (siMGL 4, siMGL 6, siMGL 15, siMGL 16 and siMGL 34) show the normal leaf phenotype. siMGL 36 shows the abnormal leaf morphology, with curled, yellowish leaves with spots of necrosis. (FIG. 3b) The tuber yields are not significantly different among all normal-looking plants, when EV (EV 5 and EV 8) and siMGL (siMGL 4, siMGL 6, siMGL 15, siMGL 16 and siMGL 34) are compared to wt (p=0.83 and 0.28, respectively, two-tailed Student's t-test). The yield of both siMGL 36 lines was the lowest of all lines harvested. Mean+/−S.E., with dots representing all data points. Two plants per genotype were sampled. Six wildtype plants were also harvested as controls. The pictures show all the harvested tubers from one representative plant in each group. Only the fully-grown tubers (on the left of each picture) were used for subsequent experiments.

(FIG. 4a) Illustration of sampling method. Tissue cylinders with diameter of 6 mm from three axes (X, Y and Z) were drilled out and different sample points along the cylinder were taken (as labeled by numbers). (FIG. 4b) Amino acid distribution gradient on the X axis, from a wildtype plant (wt), a transgenic plant with empty vector (EV), and the abnormal silencing plant (siMGL 36). The X axis on the figures represents the sample position and Y axis represents the concentration of amino acids (nmol/mg dry weight). Three tubers (as shown by three different colors) were sampled from each plant line.

(FIG. 8a) StMGLJ RNAi results in significant inhibition of StMGL1 expression in all transgenic lines, but not in empty vector control lines, compared to wildtype plants. (FIG. 8b) The free Met:Ile ratio is significantly increased in all transgenic silencing lines, but not in the empty vector controls, compared to wildtype plants. (FIG. 8c) Free Met as a proportion of all 14 amino acids quantified is significantly increased in all RNAi lines, but not in the empty vector controls, compared to wildtype plants. (FIG. 8d) The concentration of free Met is significantly increased in two transgenic silencing lines siMGL 6 and siMGL 36, but not in other transgenic lines or empty vector controls, compared to wildtype plants. (FIG. 8e) Bicinchoninic acid assays show no significant difference in protein content between wildtype and transgenic plants. (FIG. 8l) The total concentration of all 14 quantified amino acids is lower in four transgenic silencing lines (siMGL 4, siMGL 15, siMGL 16, siMGL 34) compared to wildtype plants, although not statistically significant (P>0.05).

(FIG. 9a) The correlation of StMGL1 expression with free Met:Ile ratio in all tubers. The linear regression is statistically significant (P<0.0001). (FIG. 9b) The correlation of StMGL1 expression with free Met:Ile ratio in tubers from the same plant. X axis:StMGL1 expression compared to wild type plant. Y axis: free Met:Ile ratio. EV=empty vector control, wt=wildtype, siMGL=MGL expression-silenced.

(FIG. 10a) In tissues sampled from the periphery of tubers, the ratio of free Met:Ile is significantly increased in all transgenic silencing lines, but not in the empty vector controls, compared to wildtype plants. (**P<0.002, two tailed Student's t-test). Mean+/−S.E. of n=3. (FIG. 10b) In tissues sampled from the center of tubers, the ratio of free Met:Ile is only significantly increased in two transgenic lines (siMGL 15 and siMGL 34) when compared to wildtype plants (*P<0.02, two tailed Student's t-test). Mean+/−S.E. of n=6 (wildtype) or 3 (all others). (FIG. 10c) In tissues sampled from the periphery of tubers, the concentration of free Met is significantly increased in all but one transgenic silencing line, but not in the empty vector controls, compared to wildtype plants. (*P<0.02, **P<0.002, two tailed Student's t-test). Mean+/−S.E. of n=3. (FIG. 10d) In tissues sampled from the center of tubers, the concentration of free Met is significantly increased in only one transgenic silencing line (siMGL 36) when compared to wildtype plants. (*P<0.02, two tailed Student's t-test). Mean+/−S.E. of n=6 (wildtype) or 3 (all others).

FIG. 11. An exemplary RNAi sequence useful for targeting MGL. (SEQ ID NO: 1).

DETAILED DESCRIPTION OF THE INVENTION

Figure 1:
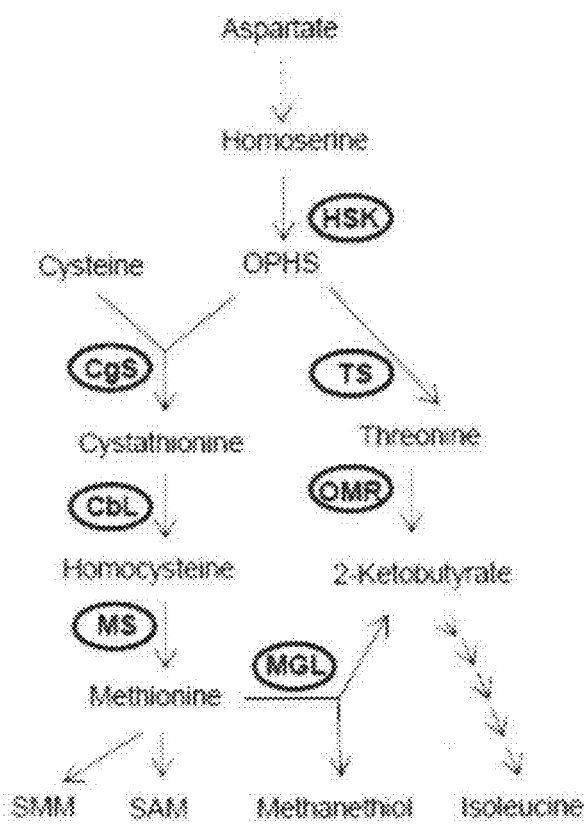
FIG. 1. Biosynthesis pathway of Met and Ile in *Arabidopsis*. Solid lines with arrows represent reactions catalyzed by one single enzyme. Dash lines with arrows indicate multiple enzymatic steps. Names of enzymes discussed in this paper are circled in ovals. HSK: homoserine kinase CgS: cystathionine γ synthase; CbL: cystathionine β lyase; MS: methionine synthase; MGL: methionine γ lyase; TS: threonine synthase; OMR: threonine deaminase; SMM: S-methylmethionine; SAM: S-adenosylmethionine; OPHS: O-phosphohomoserine FIGS. 2a and 2b. Gene models and encoded peptide sequences of StMGL1 and StMGL2.

Increasing methionine in potato tubers is desirable, both to increase the availability of this limiting essential amino acid and to enhance the aroma of baked and fried potatoes. Previous attempts to elevate potato methionine content using transgenic approaches have focused on increasing methionine biosynthesis. Higher isoleucine accumulation in these transgenic tubers suggested that the potatoes compensate for increased methionine biosynthesis with enhanced catabolism via methionine gamma-lyase (MGL) to produced 2-ketybutyrate for isoleucine biosynthesis. In accordance with the present invention, we show that potato StMGL1 encodes a functional MGL in potato tubers. In planta, silencing of StMGL1 results in increased methionine to isoleucine ratio in the free amino acid profile of potato tubers, and in some transgenic lines, elevated accumulation of free methionine. In both wildtype and transgenic tubers, the ratio of methionine to isoleucine is negatively correlated with the level of StMGL1 transcript. A three-dimensional distribution of free amino acids in potato tubers is also described.

I. Definitions

MGL is a methonine gamma lyase. The phrase "StMGL1 function" is used herein to refer to any StMGL1 activity, including without limitation expression levels of StMGL1, StMGL1 enzymatic activity, and/or modulation of essential amino acid production.

A "StMGL1 homolog" is any protein or DNA encoding the same which has similar structural properties (such as sequence identity and folding) to StMGL1.

A "transgenic plant" refers to a plant whose genome has been altered by the introduction of at least one heterologous nucleic acid molecule.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90 95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, phage or virus, that is capable of replication largely under its own control. A replicon may be either RNA or DNA and may be single or double stranded.

A "vector" is any vehicle to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide. In certain embodiments oligonucleotides can comprise primers or probes which specifically hybridize to the nucleic acid molecules of the invention. In a preferred embodiment, such probes or primers are detectably labeled. In another embodiment, the detectable label is covalently attached to the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15 to 25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "promoter region" refers to the 5' regulatory regions of a gene (e.g., CaMV 35S promoters and/or tetracycline repressor/operator gene promoters).

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic delivery, and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the nucleic acid construct in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to a genetic sequence used to transform plants and generate progeny transgenic plants. These constructs may be administered to plants in a viral or plasmid vector. Other methods of delivery such as *Agrobacterium* T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

The phrase "double-stranded RNA mediated gene silencing" refers to a process whereby target gene expression is suppressed in a plant cell via the introduction of nucleic acid constructs encoding molecules which form double-stranded RNA structures with target gene encoding mRNA which are then degraded.

The term "co-suppression" refers to a process whereby expression of a gene, which has been transformed into a cell or plant (transgene), causes silencing of the expression of endogenous genes that share sequence identity with the transgene. Silencing of the transgene also occurs.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Mature protein" or "mature polypeptide" shall mean a polypeptide possessing the sequence of the polypeptide after any processing events that normally occur to the polypeptide during the course of its genesis, such as proteolytic processing from a polyprotein precursor.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The present invention also includes active portions, fragments, derivatives and functional or non-functional mimetics of StMGL1-related polypeptides, or proteins of the invention. An "active portion" of such a polypeptide means a peptide that is less than the full length polypeptide, but which retains measurable biological activity.

A "fragment" or "portion" of an StMGL1-related polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the StMGL1-related polypeptide sequence, antigenic determinants, or epitopes are useful for eliciting immune responses to a portion of the StMGL1-related protein amino acid sequence for the effective production of immunospecific anti-StMGL1 antibodies.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immuno-affinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim, an in the latter instance, impurities ordinarily associated with the specified material(s). The term "consisting essentially of" limits the scope of a claim to the specified elements, steps or materials and those that do not materially affect the basic and novel characteristic(s) of the claimed subject matter.

II. Generation of Transgenic Crops with Increased Methionine Content by Modulation of Expression of STMGL1

The information provided herein enables the production of crops which exhibit enhanced methionine production. In one approach, transgenic potatoes will be constructed using RNA interference (RNAi) vectors. RNAi constructs targeting MGL can be expressed either constitutively or using a tuber-specific promoter. In other approaches, potatoes can be mutagenized using a chemical mutagen, e.g. ethylmethanesulfonate, and mutations knocking out MGL activity can be identified by TILLING (Targeting Induced Local Lesions IN Genomes). Targeted screening for induced mutations. McCallum C M, Comai L, Greene E A, Henikoff S. Nat Biotechnol. 2000 April; 18(4):455-7. Potato MGL can be inactivated by targeted mutagenesis using CRISPER, TALEN nuclease, or zinc finger nuclease technologies. For reference, see Targeted Mutagenesis in Zea mays Using TALENs and the CRISPR/Cas System. Liang Z, Zhang K, Chen K, Gao C. J Genet Genomics. 2014 Feb. 20; 41(2): 63-8. doi: 10.1016/j.jgg.2013.12.001. Epub 2013 Dec. 14; and ZFN, TALEN, and CRISPR/Cas-based methods for genome engineering. Gaj T, Gersbach C A, Barbas C F 3rd. Trends Biotechnol. 2013 July; 31(7):397-405. doi: 10.1016/j.tibtech.2013.04.004. Epub 2013 May 9; and Multiplex and homologous recombination-mediated genome editing in *Arabidopsis* and *Nicotiana benthamiana* using guide RNA and Cas9. Li J F, Norville J E, Aach J, McCormack M, Zhang D, Bush J, Church G M, Sheen J. Nat Biotechnol. 2013 August; 31(8):688-91. doi: 10.1038/nbt.2654.

The following materials and methods are provided to facilitate practice of the present invention.

Plant Material, Growth Conditions and Transformation

*Solanum tuberosum* cv. Désirée was vegetatively propagated from single-node stem segments in tissue culture at 22° C. under a 16 h light/8 h dark regime on CM medium (4.3 g/L Murashige and Skoog Basal Salt Mixture, 0.1 g/L myo-inositol, 0.4 mg/L thiamine HCl, 20 g/L sucrose, 8 g/L agar, adjusted to pH 5.7). Transgenic potato lines were generated by leaf transformation as described before (Van Eck et al., 2007). A 610 by fragment of StMGL1 sequence was PCR amplified by Primers ST-MGL1 NW SIL F: 5'-GGGGACAAGTTTGTACAAAAAAGCAGGCTTCAT-GAATTCGGCGAACACG-3' (SEQ ID NO: 2) and ST-MGL1 NW SIL R: 5'-GGGGACCACTTTGTA-CAAGAAAGCTGGGTCTCAGCTGCACCGC TAATGTA-3' (SEQ ID NO: 3) and cloned into the pHELLS-GATE 8 vector (Helliwell, 2003). The binary plasmid pHELLSGATE 8 MGL RNAi was introduced into *Agrobacterium tumefaciens* strain C58C1 containing pGV2260. Six-week-old transgenic and control plants were transferred from tissue culture to pots and were grown further under greenhouse conditions at 18 to 28° C. for molecular and metabolite analysis, as well as for yield tests. Tubers were sampled as described and lyophilized using a Labconco FreeZone freeze dryer (www. Labconco.com).

Amino Acid Analysis

For analysis of amino acids, fresh or lyophilized tuber samples were frozen and ground to fine powder with 3-mm steel beads using a Harbil model 5G-HD paint shaker. Ground tissue was mixed with 20 mM HCl with 40 µM of L-norleucine as an internal standard (30 µL per mg of dry tissue or 8 µL per mg of fresh tissue), the extracts were centrifuged at 14,000 rpm for 20 min at 4° C., and the supernatant was derivatized with 6-aminoquinolyl-N-hydroxysuccinimidyl carbamate (Cohen and Michaud, 1993) using an AccQ-Fluor reagent kit (Waters). During derivatization, 5-4 extracts were mixed with 35 µL borate buffer, and the reaction was initiated by the addition of 10 µL 6-aminoquinolyl-N-hydroxysuccinimidyl carbamate reagent followed by immediate mixing and incubation for 10 min at 55° C. Ten microliters of each sample were injected onto a 3.9×150-mm Nova-Pak $C_{18}$ column (Waters) using a Waters 2690 pump system, and the data were recorded using Waters Empower Software. Eluted amino acid derivatives were detected using a Waters model 2475 multi λ fluorescence detector with an excitation wavelength of 250 nm and an emission wavelength of 395 nm. Solvent A (containing sodium acetate and triethylamine at pH 5.05) was purchased premixed from Waters; Solvent B was acetonitrile:water (60:40). The gradient used was 0 to 0.01 min, 100% A; 0.01 to 0.5 min, linear gradient to 2% B; 0.5 to 15 min, linear gradient to 7% B; 15 to 19 min, linear gradient to 10% B; 19 to 32 min, 33% B; 32 to 33 min, 33% B; 33 to 34 min, 100% B, 34 to 37 min, 100% B. Flow rate was 1.0 mL min$^{-1}$. Standard curves were prepared using amino acids purchased from Sigma-Aldrich.

RNA Isolation and Real-time PCR

RNA was extracted from lyophilized potato tuber powders according to (Kumar et al., 2007), with modifications. About 25 mg of dry tissue powder was mixed with 1 mL of extraction buffer. To make 1 ml of extraction buffer, sequentially add 0.2 mL of 5 M NaCl, 0.33 mL of 1.95% $Na_2SO_3$, 0.35 mL of borate-Tris buffer (10 mM EDTA with 0.2 M boric acid, adjusted to pH 8.0 by Tris base), 0.1 mL 10% SDS and 0.02 mL of beta-mercaptoethanol. Samples with buffer were mixed by shaking and incubated at 65° C. for 5 min, before centrifugation at 15,000 g for 5 min. One mL of supernatant was transferred to a new tube, to which 1 mL of acid phenol:chloroform:isoamyl alcohol (100:20:1) was added, mixed and centrifuged at 10,000 g for 4 min. 0.95 mL of supernatant was transferred to another new tube, with addition of equal volume of chloroform:isoamyl alcolol (25:1). After centrifugation at 10,000 g for 4 min, 0.7 mL of supernatant was transferred to a new tube and mixed with 0.63 mL of isoproponal. The mixture was kept at 4° C. for 60 min and then centrifuged at 15,000 g for 20 min at 4° C. The pellet was dissolved in 100 µL of RNase free water. To specifically precipitate RNA, 30 µL of 8M LiCl was added and samples were kept at −20° C. for 30 min. The pellet was washed with 0.5 mL 70% ethanol and dissolved in 80 µL of RNase free water. To remove residual DNA, DNase I from Sigma (AMPD1) was used to treat all RNA according to the instruction from the manufacturer. Finally, the presence (of the lack of) DNA was checked by PCR reactions using the primer set: Genomic_F: 5'-GCACCAATCCAGGT-GAAATC-3' (SEQ ID NO: 4) and Genomic_R: 5'-GTG-GTCTTTCGGTATTTAAG-3' (SEQ ID NO: 5).

DNA-free total RNA was converted into cDNA using oligo-dT20 primers, 10 mM dNTPs, and Clontech SMART™ MMLV Reverse Transcriptase (Clontech, http://www.clontech.com/) according to the manufacturer's instructions and the final product was diluted 3 times in RNase-free water. Q-RT-PCR analysis was done in optical 384 well clear optical reaction plates and optical adhesive covers (Applied Biosystems, http://www.appliedbiosystems.com/) with an ABI 7900HT Fast Real-Time PCR System (Applied Biosystems), using SYBR Green to monitor double-stranded DNA synthesis. Each reaction contained 1 µL of cDNA, 0.5 µL of each of the two gene-specific primers (10 pmol $\mu L^{-1}$), and 5 µL of 2×SYBR Green PCR mix reagent (Applied Biosystems) in a final volume of 10 µL. The following PCR program was used for all PCR reactions: 95° C. for 2 min, followed by 40 cycles of 95° C. for 15 s, 53° C. for 30 s and 72° C. for 30 s. A dissociation curve was obtained at the final step to determine if only one product was formed. Threshold cycle (Ct) values were calculated using Applied Biosystems Software (SDS version 2.3, for Windows XP). Subsequently, Ct values were normalized for differences in dsDNA synthesis using the StEF1α Ct values. The following primers were used: StEF1α_F: 5'-TGCT-GCTGTAACAAGATGG-3' (SEQ ID NO: 6) StEF1α_R: 5'-ATTTTGTCAGGGTTGTAACC-3' (SEQ ID NO:7) StMGL1_F: 5'-TGA TATCATTGCAGGTGCT-3' (SEQ ID NO:8) StMGL1_R: 5'-TGCAAGTTCAAAGGCCAC-3' (SEQ ID NO: 9) StMGL2_F: 5'-CAA ATATATT-AGTGGGGCTGCC-3' (SEQ ID NO: 10) StMGL2R: 5'-ATCTTAGCATTCATGGTTGG-3' (SEQ ID NO: 11)

Quantification of Total Protein

Total protein was extracted from lyophilized tuber powder using 65 mM Tris pH 6.8 with 2% SDS (1 mL for 15 mg dry powder). The protein concentration in the extract was measure by BCA Protein Assay Kit from Pierce (www.piercenet.com) on a Bio-Tek Synergy 2 plate reader according to the user manuals.

The following example is provided to illustrate certain embodiments of the invention. It is not intended to limit the invention in any way.

EXAMPLE I

The Catabolic Enzyme Methionine Gamma Lyase

Limits Methionine Accumulation in Potato Tubers

Met biosynthesis has been studied extensively in *Arabidopsis thaliana* (*Arabidopsis*). Homoserine kinase catalyzes the formation of O-phosphohomoserine (OPHS), which serves as a precursor for both Met and threonine (Thr) biosynthesis (FIG. 1); for reviews, see (Amir et al., 2002; Hesse et al., 2004; Jander and Joshi, 2010). In one branch of the pathway, OPHS is converted to Thr by Thr synthase. In the other branch, cystathionine γ-synthase (CgS) catalyzes the formation of cystathionine from OPHS and cysteine. Cystathionine is further converted into homocysteine by cystathionine β-lyase. Finally, Met synthase catalyzes the last step of Met biosynthesis using the substrates homocysteine and methyltetrahydrofolate. Since Thr synthase and CgS compete for a common substrate, the relative activity of these two enzymes is critical for regulating the balance of Thr and Met biosynthesis. In *Arabidopsis*, the overall abundance these two amino acids is limited by homoserine availability rather than homoserine kinase activity (Lee et al 2005).

In addition to direct competition with Thr biosynthesis, Met biosynthesis is regulated by several other mechanisms in *Arabidopsis*. One of the major downstream products of Met, S-adenosylmethionine (SAM), feedback-activates Thr synthase, thus indirectly reducing the flux to CgS (Curien et al., 1998). The *Arabidopsis* CgS (MTO1) expression is negatively regulated by Met or other downstream products at the level of mRNA stability (Chiba et al., 1999; Onouchi et al., 2005). However, the regulatory domain in the coding region, as well as the negative feedback control, is absent in potato CgS (Kreft et al., 2003). Met biosynthesis also is under developmental control, as the gene expression and metabolite accumulation vary in different tissues and developmental stages (Bartlem et al., 2000; Kim et al., 2002).

Based on these findings, several approaches have been taken to increase Met levels in potato tubers by genetic engineering. Transgenic expression of *Escherichia coli* homoserine kinase, the committing enzyme for Thr and Met biosynthesis (FIG. 1), increased activity of this enzyme more than ten-fold in potatoes, but did not increase tuber methionine content (Rinder et al., 2008). Antisense inhibition of Thr synthase caused free Met accumulation, but the plants were severely stunted, likely due to insufficient Thr (Zeh et al., 2001). Increasing the expression of CgS in potato produced mixed results in three separate studies. Overexpression of potato CgS had no significant effects on tuber Met levels (Kreft et al., 2003), likely due to gene silencing and/or feedback regulation of the enzyme. Overexpression of *Arabidopsis* CgS increased the tuber Met levels, although the results varied among growth conditions (Di et al., 2003). In another case, overexpressing feedback-insensitive *Arabidopsis* CgS produced morphologically abnormal potato plants with very low yields (Dancs et al., 2008). Nevertheless, although the final accumulation of Met is determined by both its synthesis and catabolism, these previous efforts have been focused only on the increasing the biosynthesis.

Plants possess three major Met catabolic pathways (FIG. 1): (i) A significant amount of Met is converted to S-adenosylmethionine (SAM), which serves as a precursor for ethylene biosynthesis and acts as a methyl group donor in many plant biosynthetic and regulatory pathways. (ii) Met can be converted to S-methylmethionine (SMM), a major sulfur transport metabolite plants (Bourgis et al., 1999). (iii) Met can be broken down to methanethiol and 2-ketobutyrate by Met gamma-lyase (MGL). In turn, 2-ketobutyrate is a precursor for isoleucine (Ile) biosynthesis via five enzymatic steps (FIG. 1) (Joshi and Jander, 2009; Rébeillé et al., 2006). Inhibition of these Met catabolic pathways thus provides an opportunity to manipulate Met accumulation in plants. For example, the mto3 mutation in an *Arabidopsis* causes increased accumulation of free Met by reducing the activity of SAM synthase (Shen et al., 2002).

Among the three major Met catabolic pathways, MGL is an attractive target for genetic engineering. As 2-ketobutyrate also can be synthesized from Thr by Thr deaminase (OMR1), MGL inhibition will not entirely shut down the Ile biosynthesis pathway (Mourad and King, 1995). Although the function of plant MGL has only been verified in *Arabidopsis*, there is likely a similar Met catabolic pathway in potato. It is noteworthy that, among prior studies to increase tuber Met accumulation, two that also quantified the content of other amino acids (Dancs et al., 2008; Zeh et al., 2001) show an Ile increase. This suggested that Met accumulation in potato tubers may be limited by MGL catabolism to produce Ile, and provided the impetus for the present research to identify the potato MGL and increase free Met levels in potato cv. Desiree by reducing MGL expression using an RNA interference (RNAi) approach.

Results

Generation of Transgenic Potato Plants with an MGL RNAi Construct

Figure 2A:
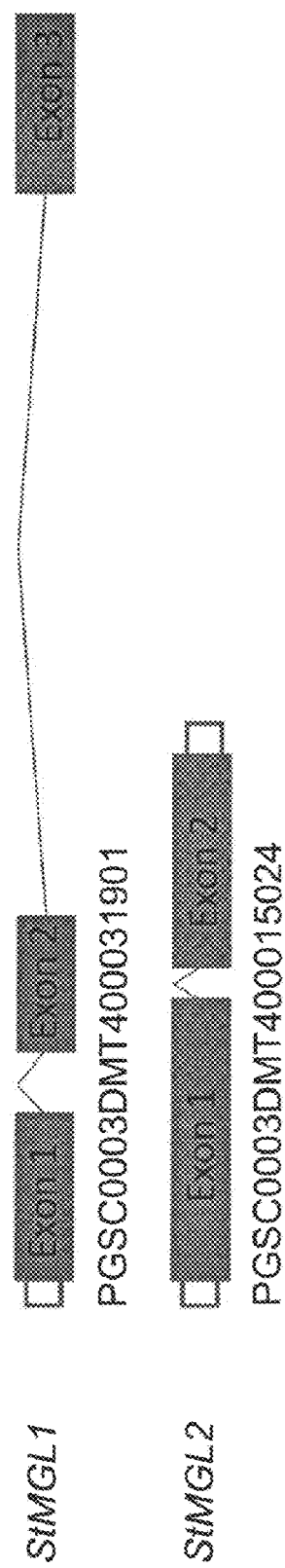
(FIG. 2a) Gene models for mRNA of StMGL1 and StMGL2. Open box: untranslated region (UTR); Filled box: exon; Connecting lines: intron.
Figure 2B:
(FIG. 2b) Sequence alignment of three proteins: StMGL1 (SEQ ID NO: 12), StMGL2 (SEQ ID NO: 13) and AtMGL (SEQ ID NO: 14) using ClustalW (www.clustal.org). Identical sequences are marked with dark shading (when shared by all three proteins) or light shading (when shared by only two proteins).

To identify potato MGL genes, *Arabidopsis* MGL (AT1G64660.1) was used to BLAST search the doubled monoploid potato genome at the Solanaceae Genomics Network (www.solgenomics.net (Bombarely et al., 2011)). This identified two mRNA sequences (PGSC0003DMT400031901 and PGSC0003DMT400015024) that encode proteins with 72% and 74% amino acid identity, respectively, to *Arabidopsis* MGL, and 82% sequence identity to one another (FIG. 2). These two genes were designated as StMGLJ and StMGL2, though they are annotated as CgS genes by the potato genome project. However, unlike StMGLJ which has EST (Genbank ID: CK276817.1) data supporting its expression, there is no evidence for StMGL2 expression in potato tubers and this gene is expressed at a very low level, if at all, in other tissues. To generate an RNAi construct targeting StMGLJ, 610 bp of the StMGL1 cDNA sequence were amplified by PCR and cloned into the pHELLSGATE 8 vector, thereby generating a hairpin structure of the cloned sequence (Helliwell, 2003; Wesley et al., 2001). This hairpin sequence, when expressed under the constitutive cauliflower mosaic virus 35S promoter in potato plants, should reduce the expression level of endogenous StMGLJ, including in tubers and stolons. Control plants were transformed with the empty vector.

Figure 3A:
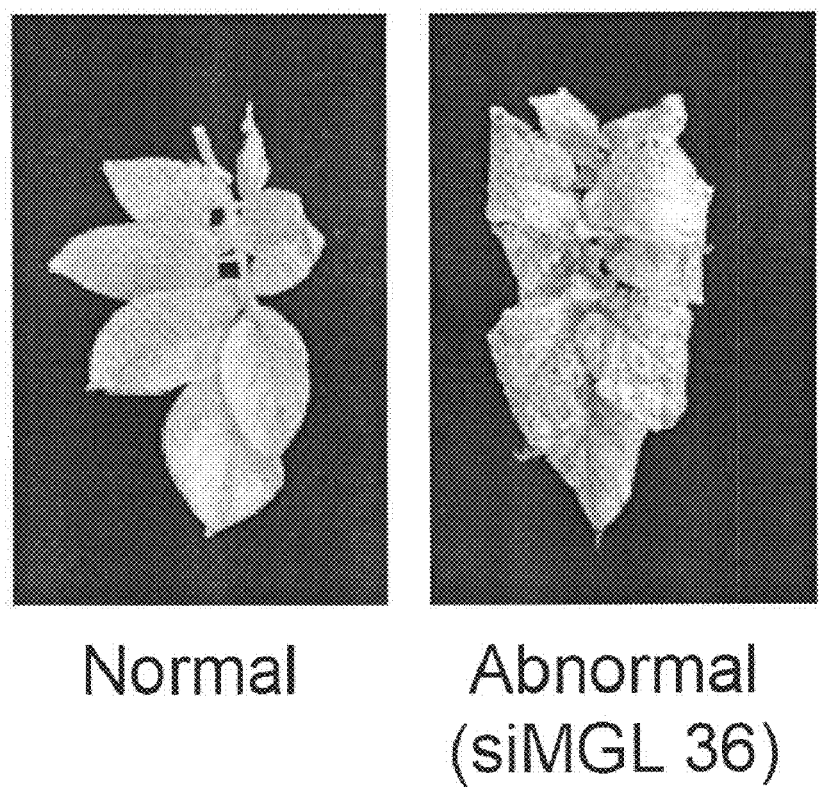
FIGS. 3a and 3b. Growth and yield phenotypes of plant lines.
Figure 3B:
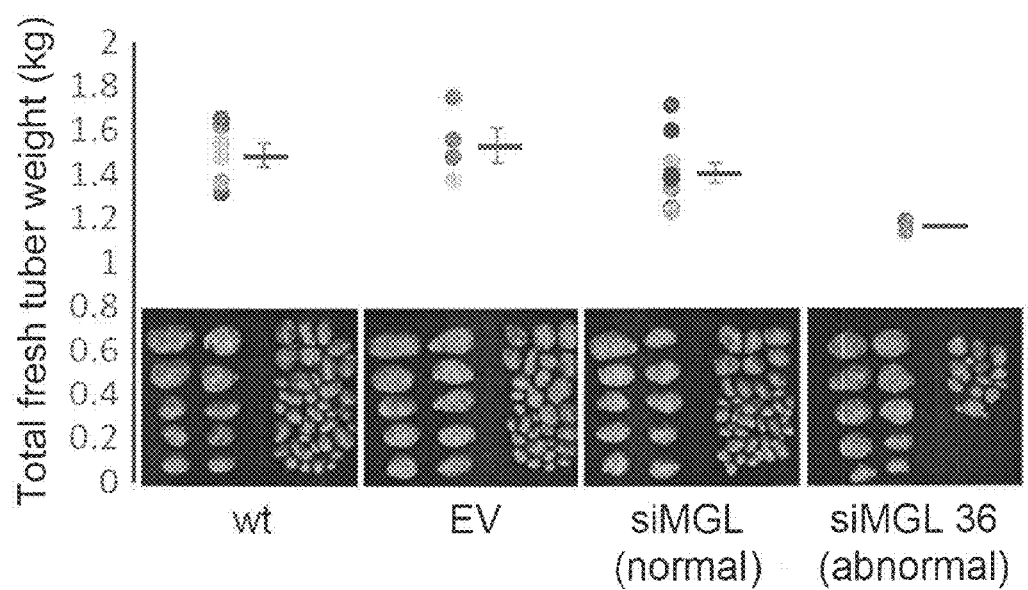

All transgenic MGL-silenced (siMGL) and control plantlets were genotyped and moved from tissue culture to soil, grown for 5 months in a greenhouse, and then harvested for tuber analysis. Five transgenic silencing lines appeared normal, but one line, siMGL 36, showed significant differences in morphology and growth compared to non-transgenic and empty vector controls. Leaves of siMGL 36 had spots of necrosis and were yellowish and curled compared to the non-transgenic controls (FIG. 3A). With the exception of siMGL 36, there was no significant difference in tuber yield between the siMGL plants and non-transgenic or empty vector control potato plants (FIG. 3B).

Free Amino Acids are More Enriched in the Center of Potato Tubers

Figure 4A:
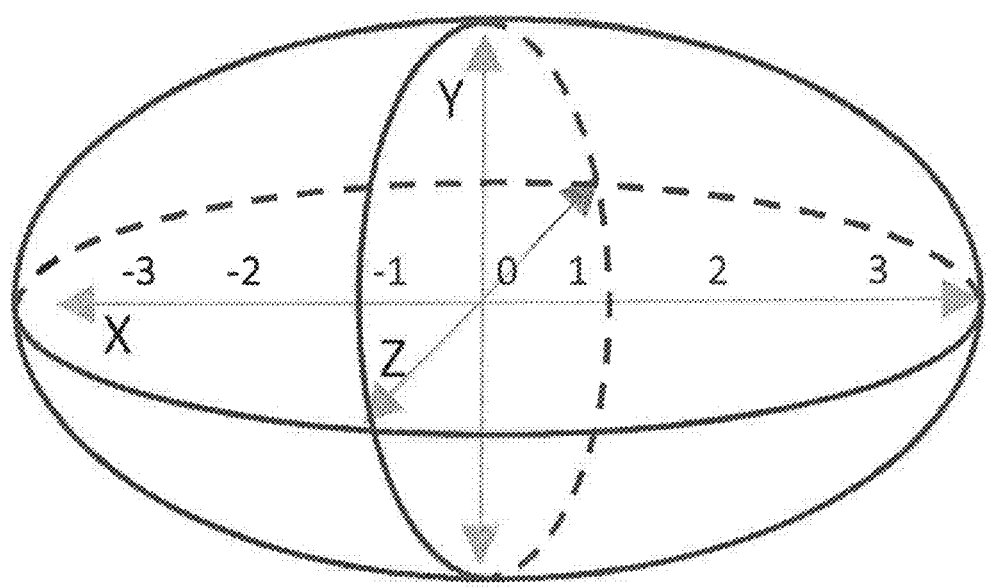
FIGS. 4a and 4b. Three dimensional distribution of free amino acids in potato tubers.
Figure 4B:
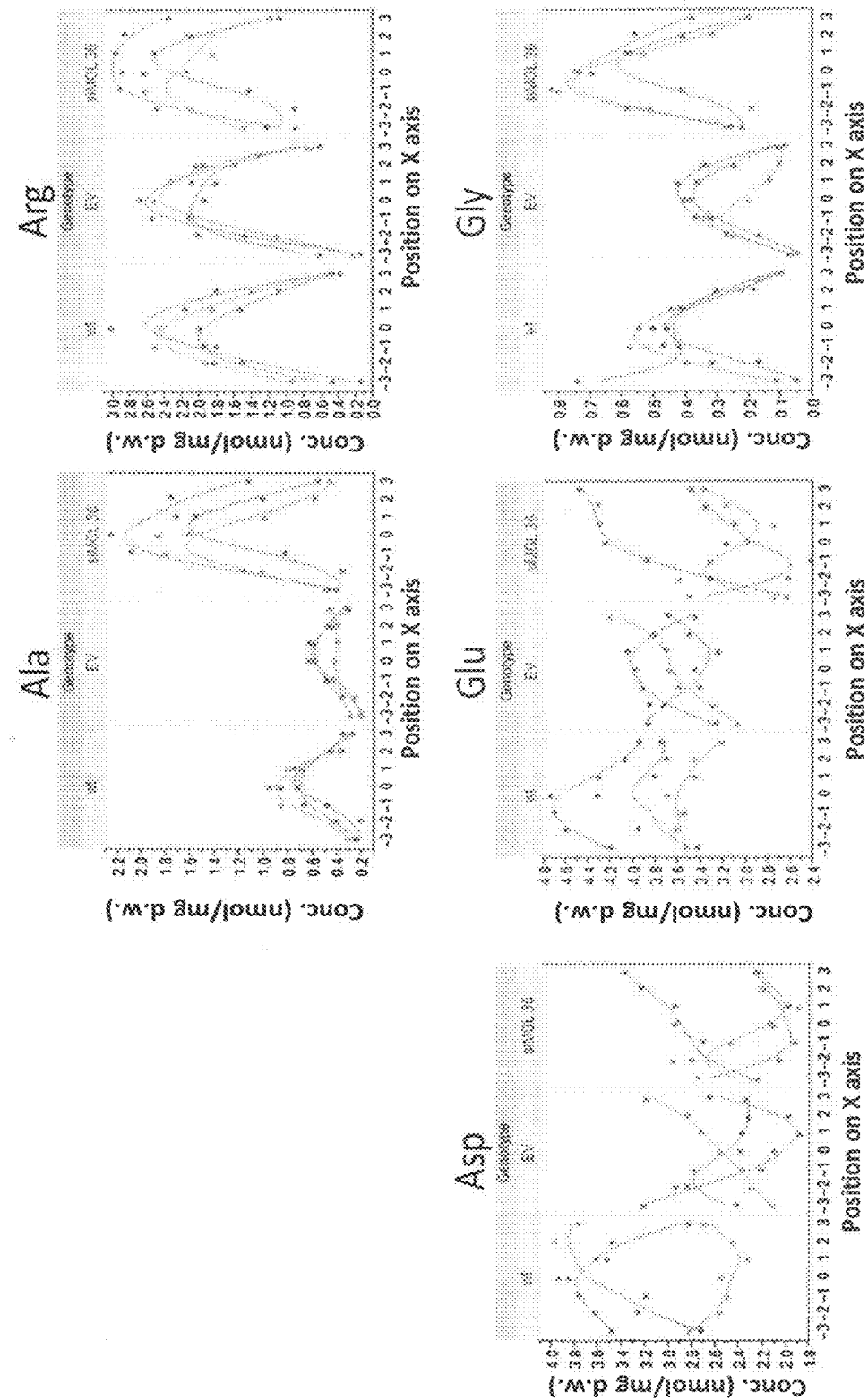
Figure 4B:
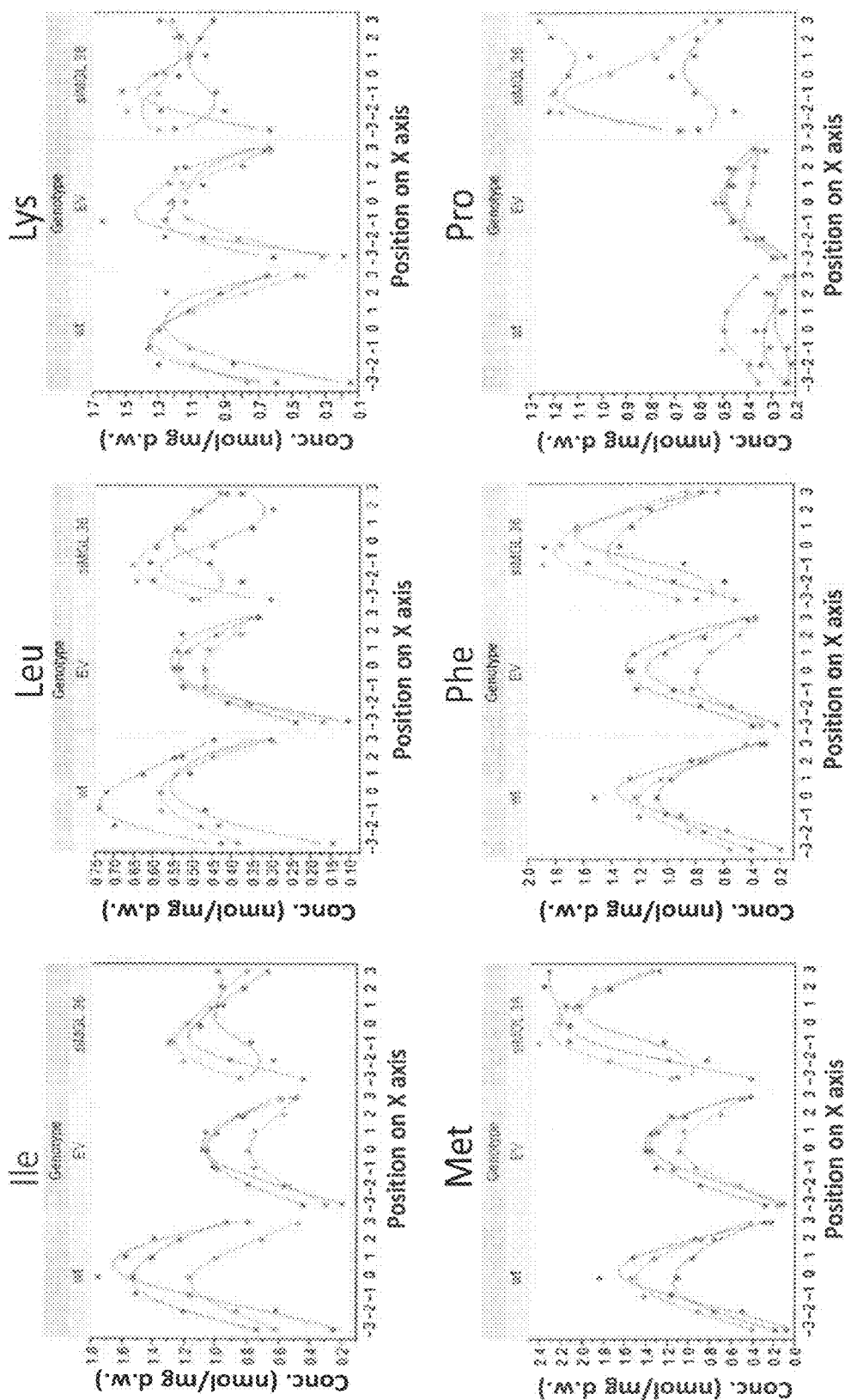
Figure 4B:
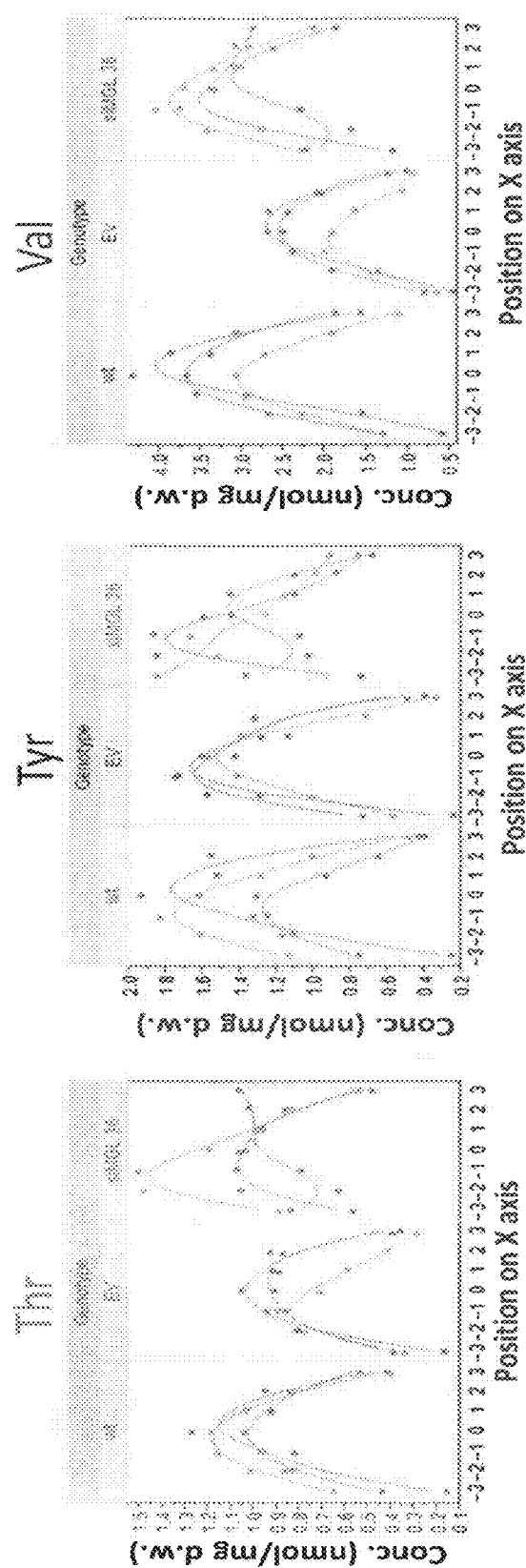
Figure 5:
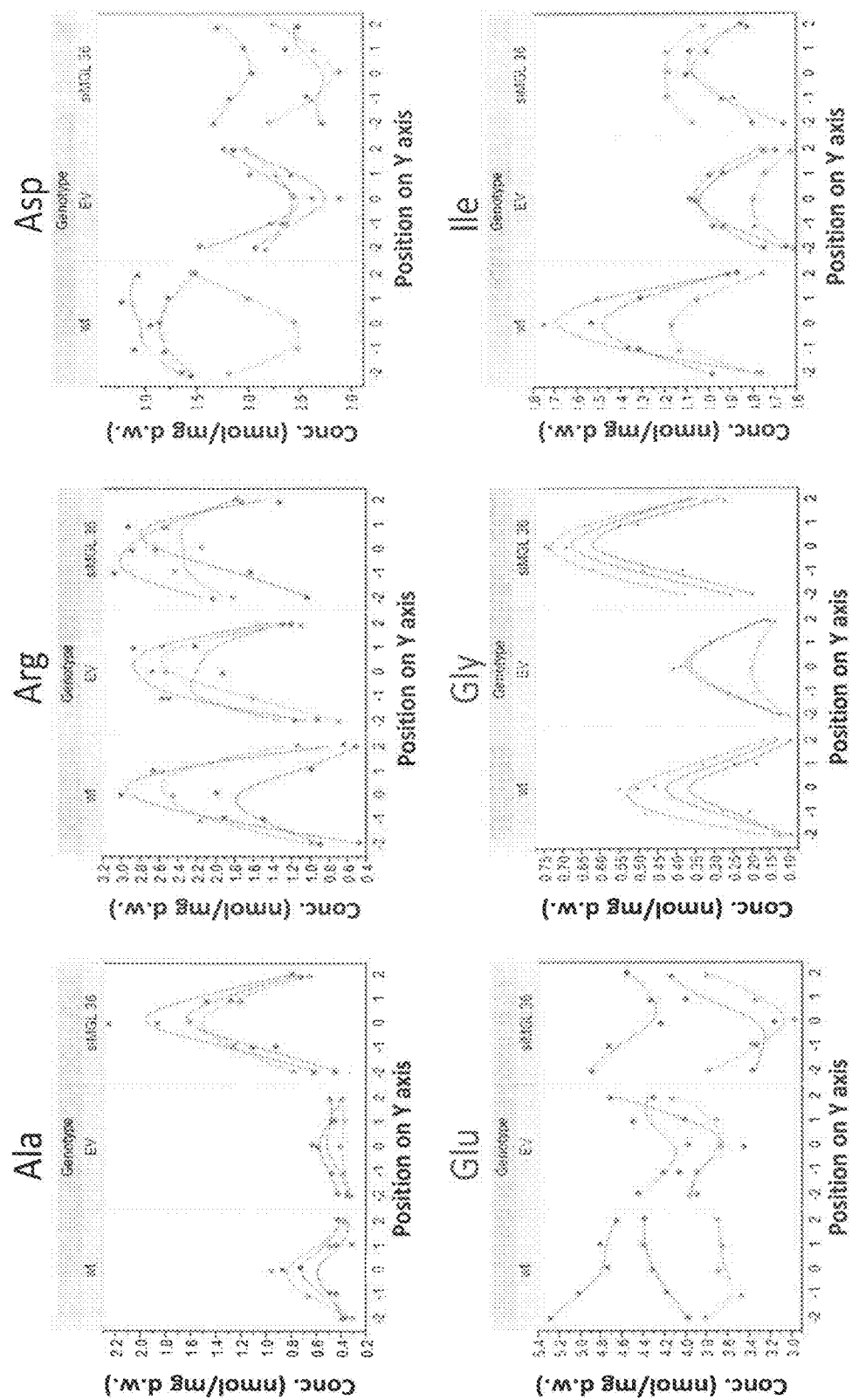
FIG. 5. Three dimensional distribution of free amino acids inside potato tubers (Y axis). Amino acid distribution gradient on the Y axis, as illustrated in FIG. 4A, from a wildtype plant (wt), a transgenic plant with empty vector (EV) and the abnormal silencing plant (siMGL 36). The X axis in the figures represents the sample position and the Y axis represents the concentration of amino acids (nmol/mg dry weight). Three tubers (as shown by three different colors) were sampled from each plant line.
Figure 5:
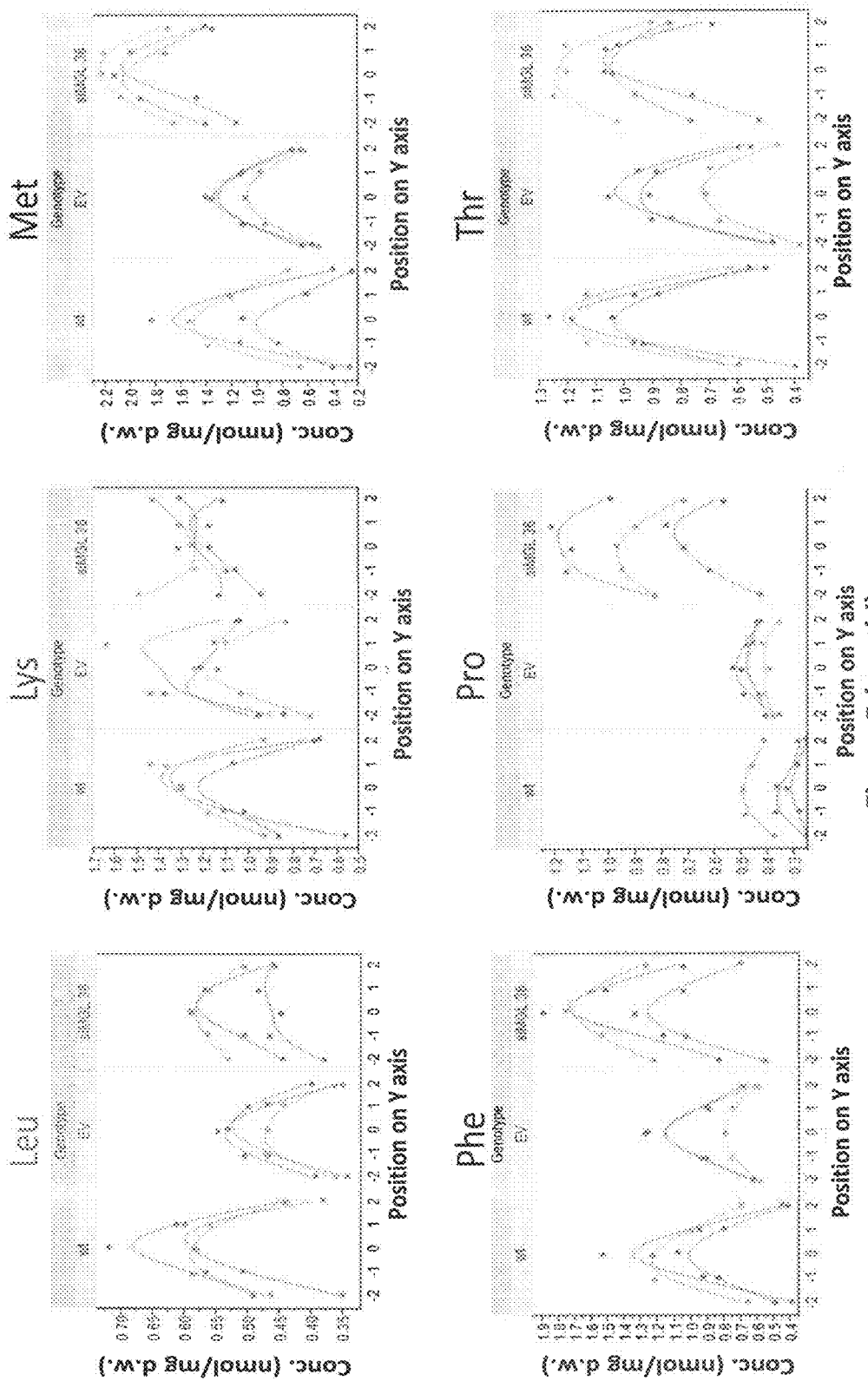
Figure 5:
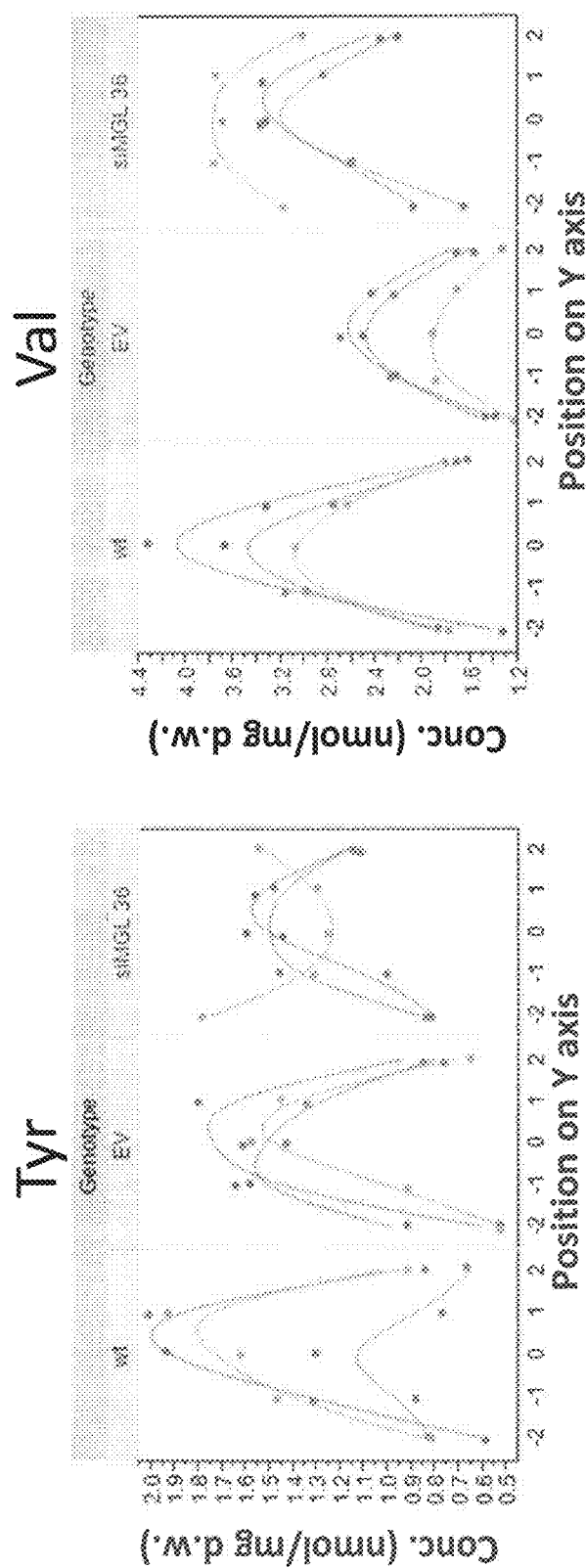
Figure 6:
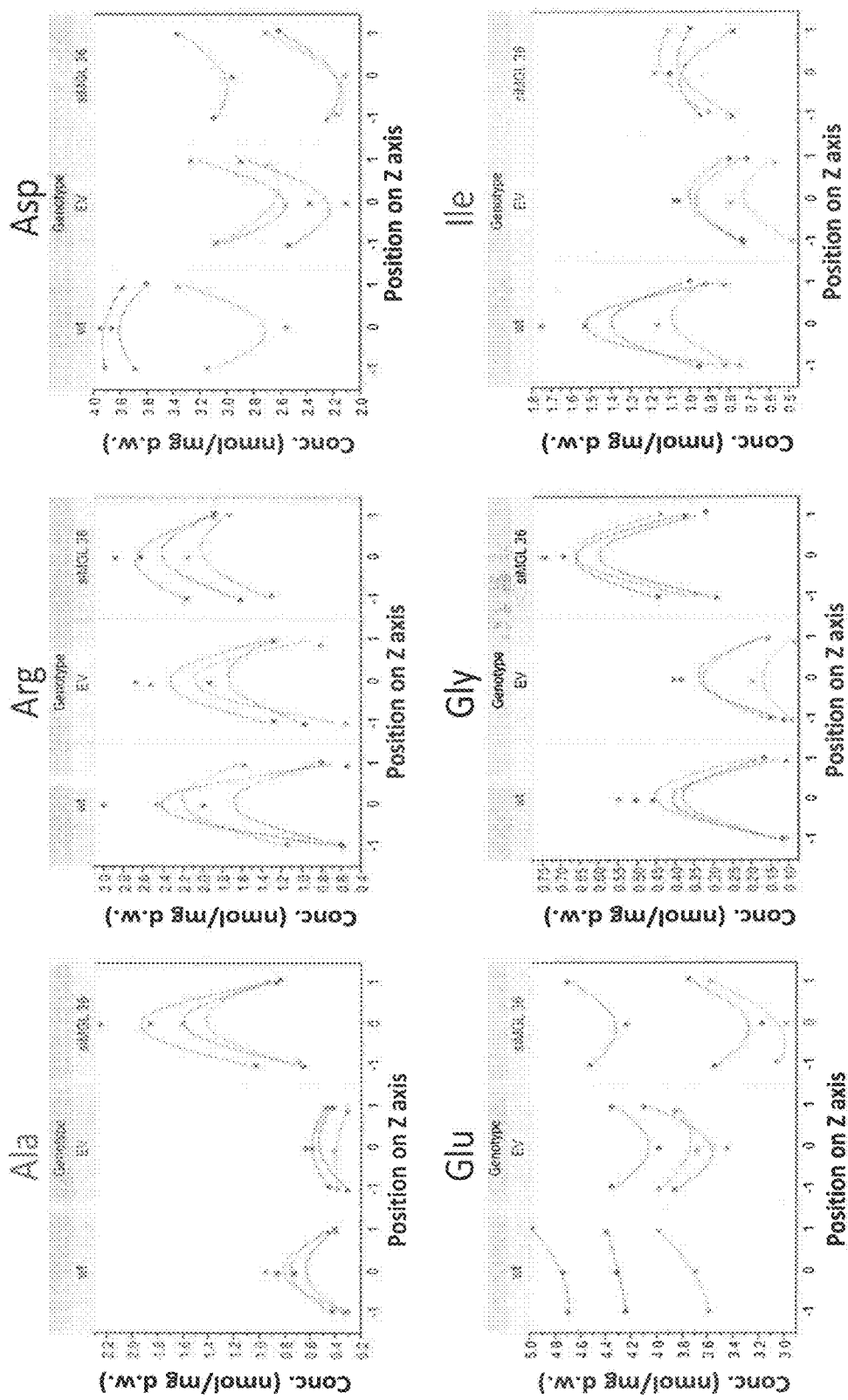
FIG. 6. Three dimensional distribution of free amino acids inside potato tubers (Z axis). Amino acid distribution gradient on the Z axis, as illustrated in FIG. 4a, from a wildtype plant (wt), a transgenic plant with empty vector (EV) and the abnormal silencing plant (siMGL 36). The X axis on the figures represents the sample position and the Y axis represents the concentration of amino acids (nmol/mg dry weight). Three tubers (as shown by three different colors) were sampled from each plant lines.
Figure 6:
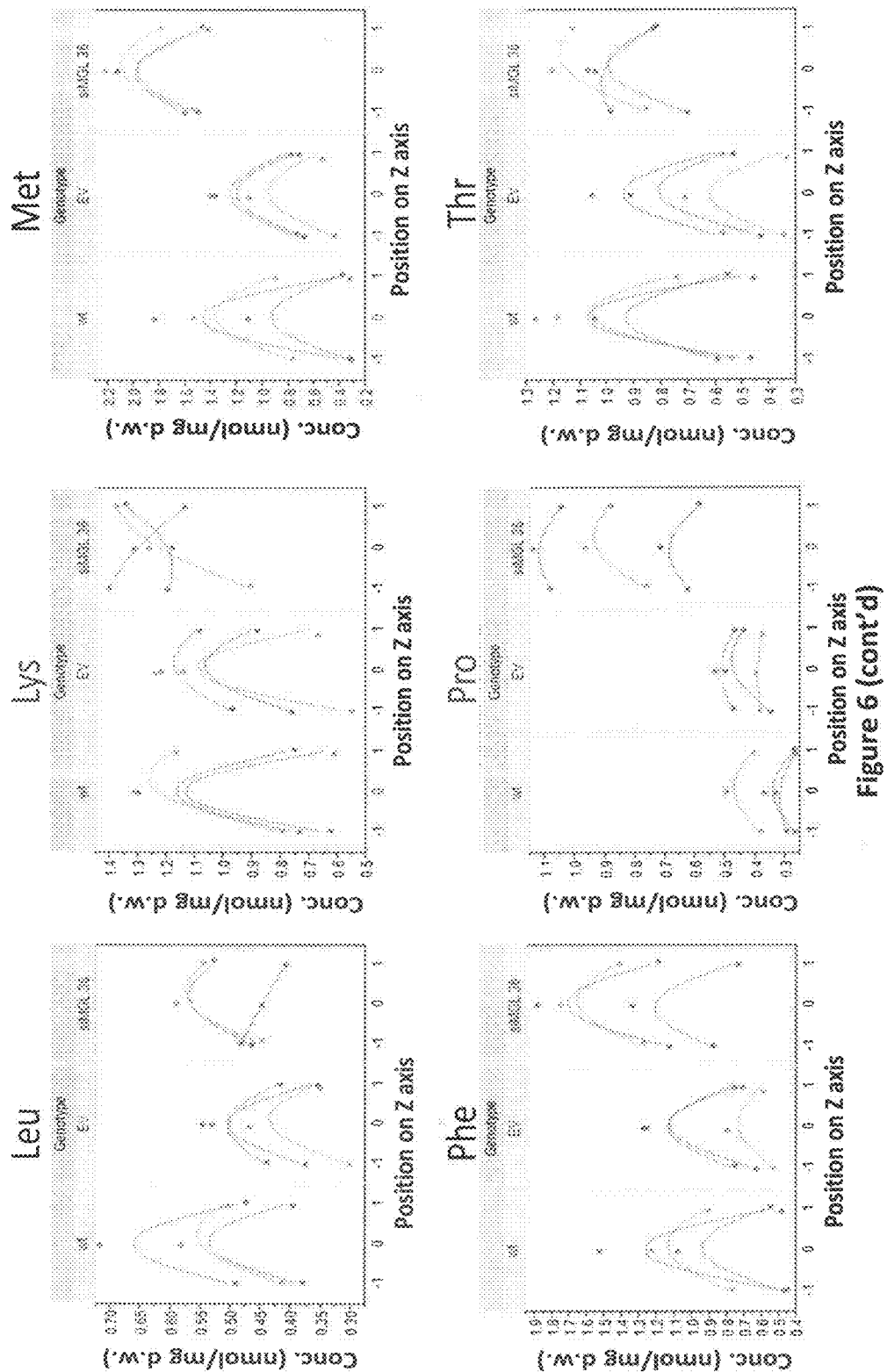
Figure 6:
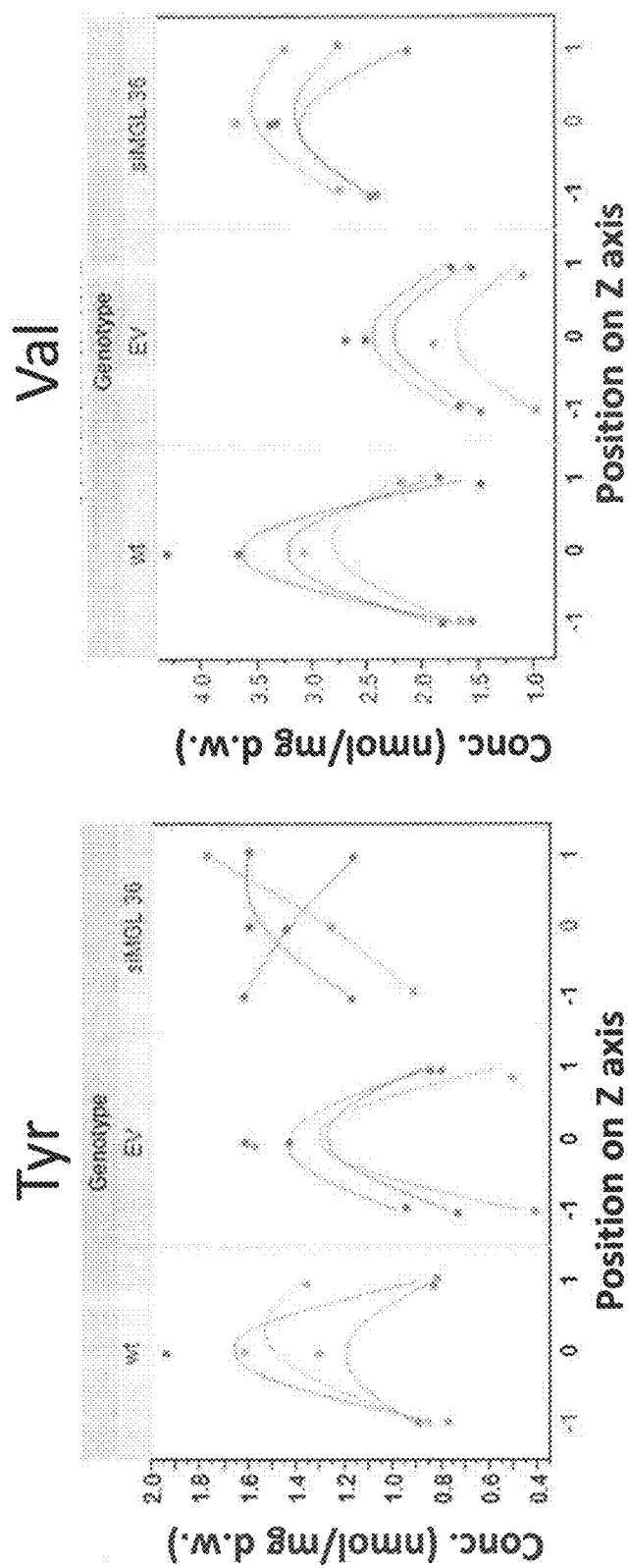
Figure 7:
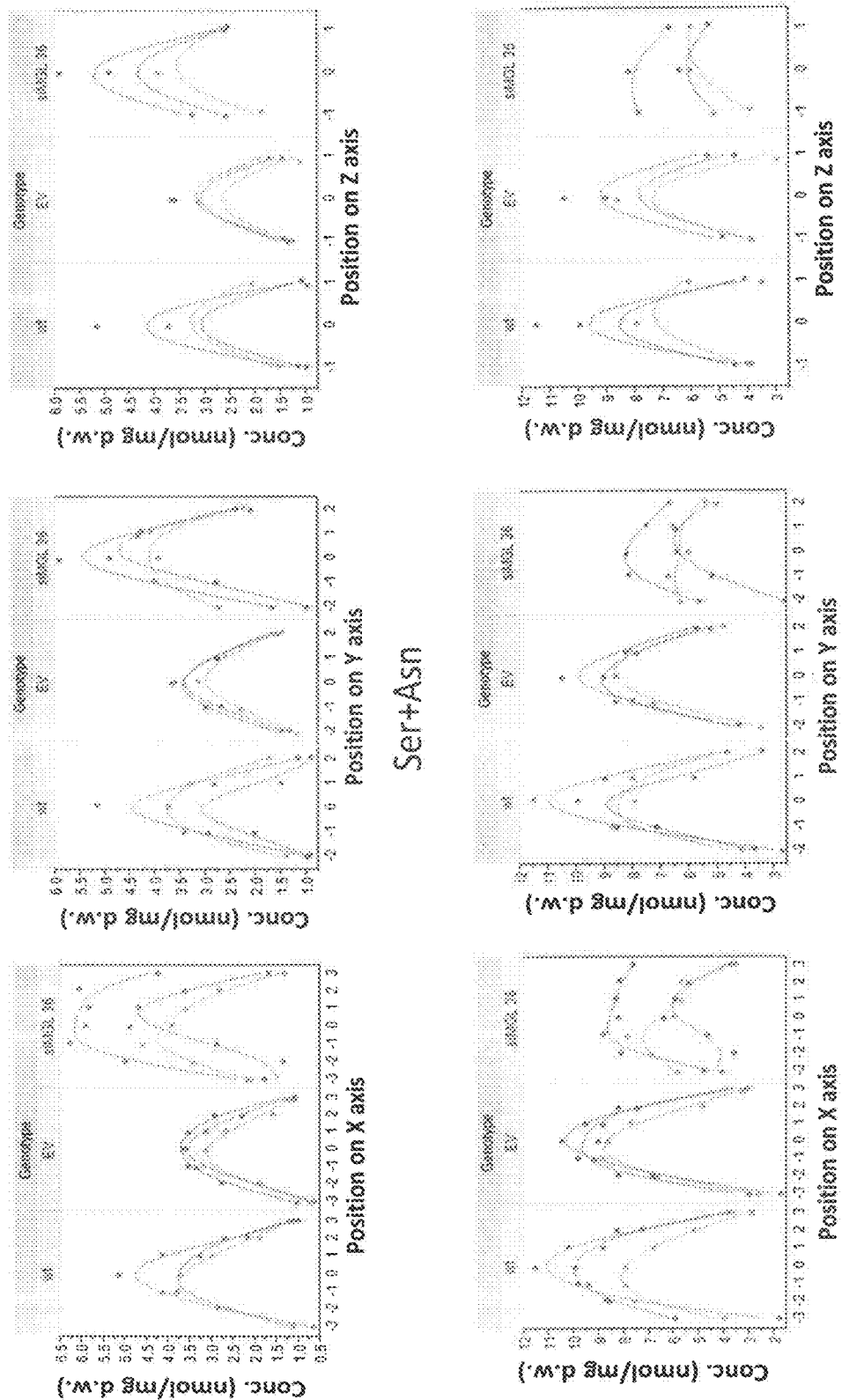
FIG. 7. Three dimensional distribution of other amino acids inside potato tubers. Amino acid distribution gradient on the X, Y and Z axes, as illustrated in FIG. 4A, from a wildtype plant (wt), a transgenic plant with empty vector (EV) and the abnormal silencing plant (siMGL 36). The X axis in the figures represents sample position and the Y axis represents the concentration of amino acids (nmol/mg dry weight). Three tubers (as shown by three different colors) were sampled from each plant lines. As His and Ser cannot be clearly separated from Gln and Asn, respectively, in our analysis, the concentration is an estimate.

An individual potato plant generally produces many tubers with different sizes, shapes, and metabolite levels. Even inside a single tuber, the abundance and distribution of metabolites can vary (Hoza et al., 2010). To examine the amino acid variation within individual tubers, we analyzed three tubers from each of three representative transgenic and non-transgenic potato lines. Free amino acid concentration in the peel was determined to be less than in tuber flesh and the total amino acids in the peel make only a small contribution to overall amino acid content given the weight of the peel is much less than the flesh. Therefore, we focused subsequent amino acid analysis on the tuber interior. After removal of the peels, cylindrical samples were drilled from three axes: X, Y and Z, which are perpendicular to each other and cross at the center of the potato tuber (FIG. 4A). X is the longest and Z is the shortest axis across the tuber. Small sections of tuber flesh were cut out from the center and the sides of all three axes (three from each side of X, two from each side of Y and one from each side of Z). The X represents the axis from the stolon attachment point (−3) to the bud side (3). Amino acid analysis of these samples showed that most free amino acids are not evenly distributed inside potato tubers, but rather are more concentrated at the center compared to the periphery. FIG. 4B shows a representative data set: fourteen amino acid gradients along the X axis of tubers from a wild type plant (wt), an empty vector transgenic control line (EV) and the siMGL 36 silencing line. All quantified amino acids, except for Asp and Glu, display a clear gradient that peaks at the center of the tubers and becomes lower at the periphery. The Y and Z axes show similar patterns and can be found in FIGS. 5 and 6. For example, free methionine concentration in the center of potato tuber was generally twice as high as in the region just under the skin. His and Ser peaks could not be clearly separated from Gln and Asn, respectively, in our HPLC gradient so the total peak areas of the merged peaks were used to show the distribution of the combined amino acids, which also reaches its highest point at the tuber center (FIG. 7). Based on this observation, we sampled tissue across all three axes in subsequent experiments to better represent the actual amino acid content in an entire tuber. For each tuber analyzed, all three cylinders from three axes were drilled, lyophilized, and combined into one sample for use in RNA, protein, or amino acid extraction.

Figure 8A:
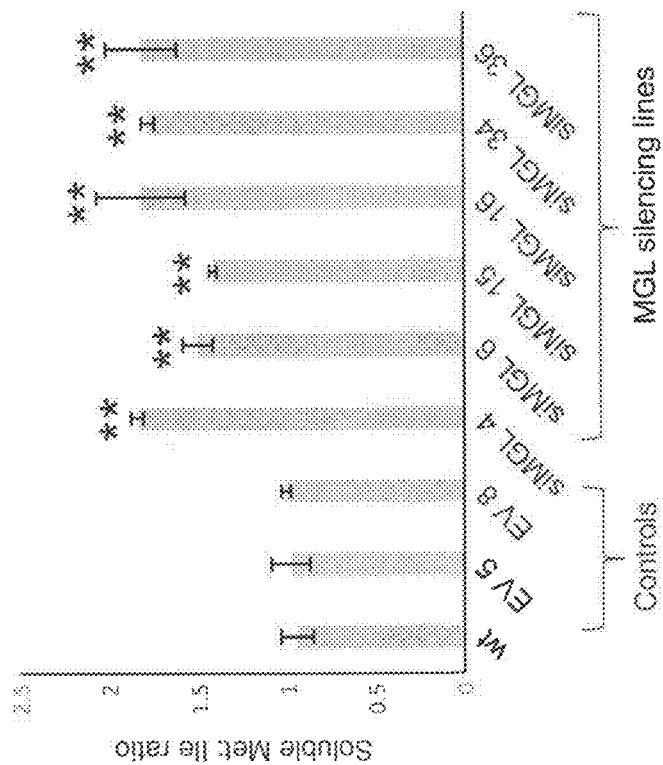
FIGS. 8a-8f. StMGLJ expression silencing and its effects on Met and Ile accumulation For all figures: *P<0.02, **P<0.002, two tailed Student's t-test. Mean+−S.E. n=8 (wildtype) or 4 (all other genotypes).
Figure 8B:
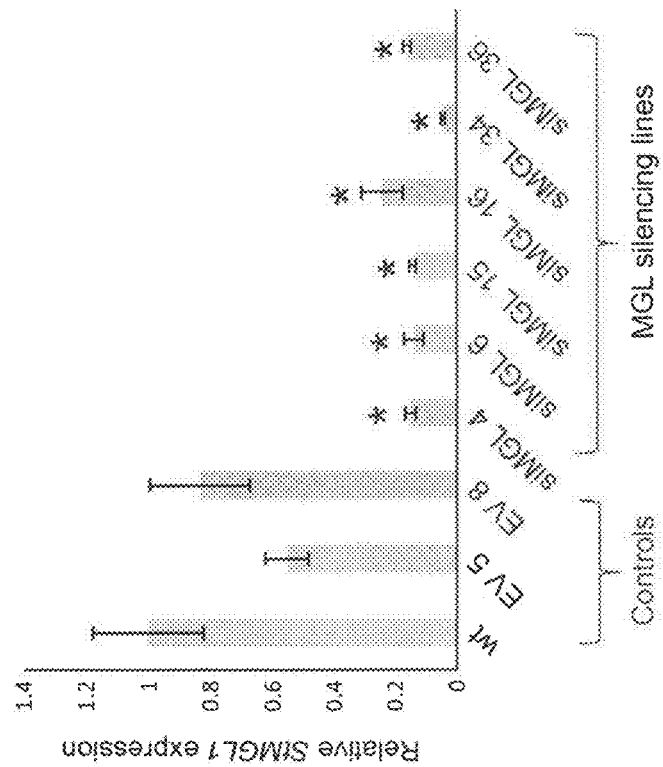

Inhibition of StMGL1 Expression Significantly Increases Met/Ile Ratio in Potato Tubers To measure the efficiency of StMGL1 gene silencing in the transgenic plants, RNA was extracted from the sample powder described above. A potato elongation factor 1 alpha subunit (StEF1a GenBank: AB061263) was used as the internal control gene due to its stable expression in potato tubers (Nicot, 2005). Real-time quantitative PCR revealed that expression of StMGL1 in tubers of all 6 transgenic StMGL-silenced plants is significantly lower than in non-transgenic control plants, ranging from 4% to 25% of the wildtype expression levels. Although there was a trend toward lower StMGL1 in empty vector transgenic controls this difference is not statistically significant (FIG. 8A).

It is possible that StMGL2 would be upregulated in StMGL1-silenced plants to compensate for the reduced enzymatic activity. Therefore, StMGL2 expression was monitored in the same assay. However, StMGL2 expression could not be reliably quantified and was consistently less than 0.003% of StEF1a expression. These results suggest that StMGL2 is expressed at a very low level, if at all, in potato tubers and is not functionally up-regulated to compensate for the loss of StMGL1 in RNAi plants.

Figure 8D:
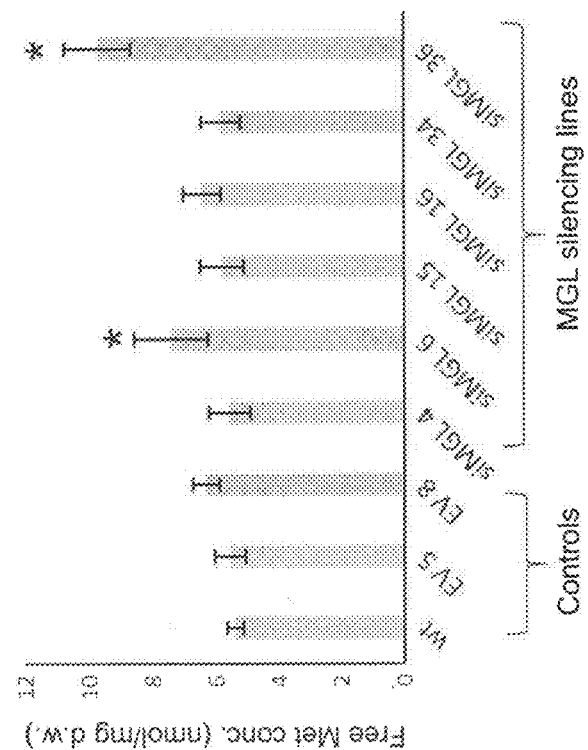
Figure 8C:
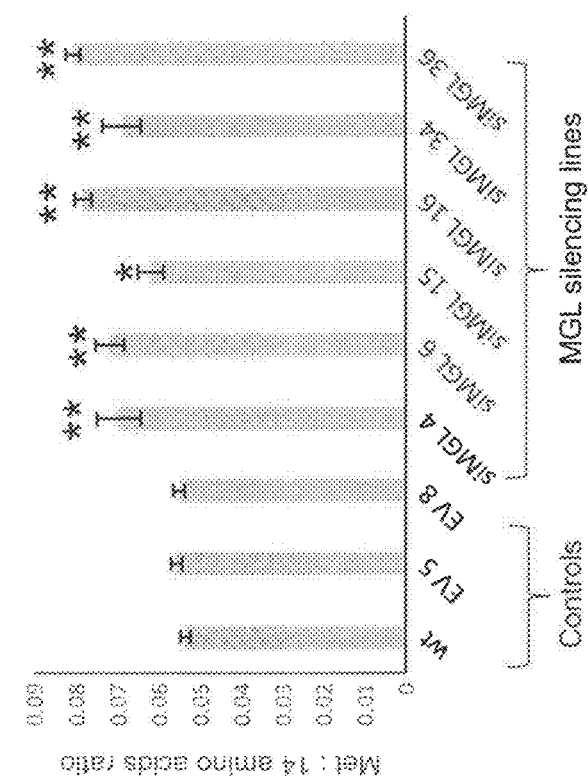
Figure 8F:
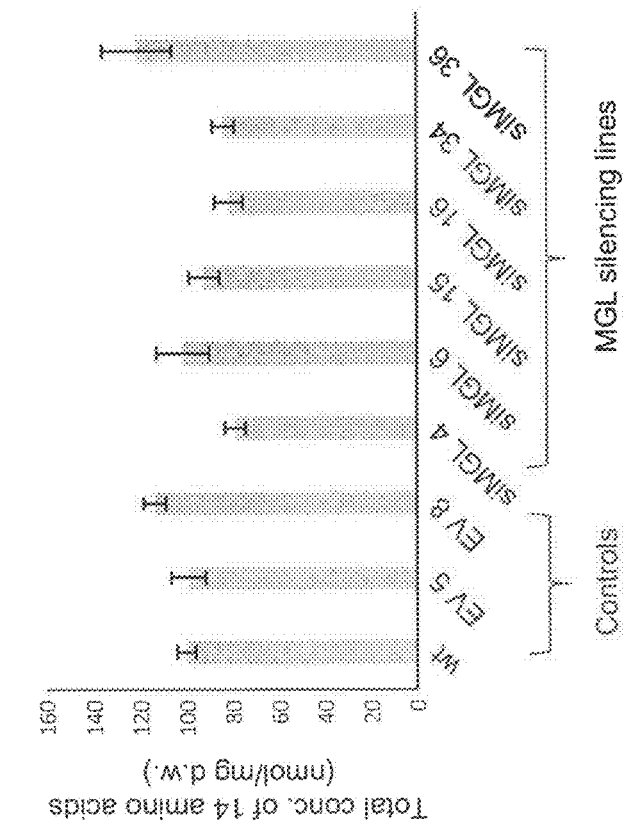
Figure 8E:
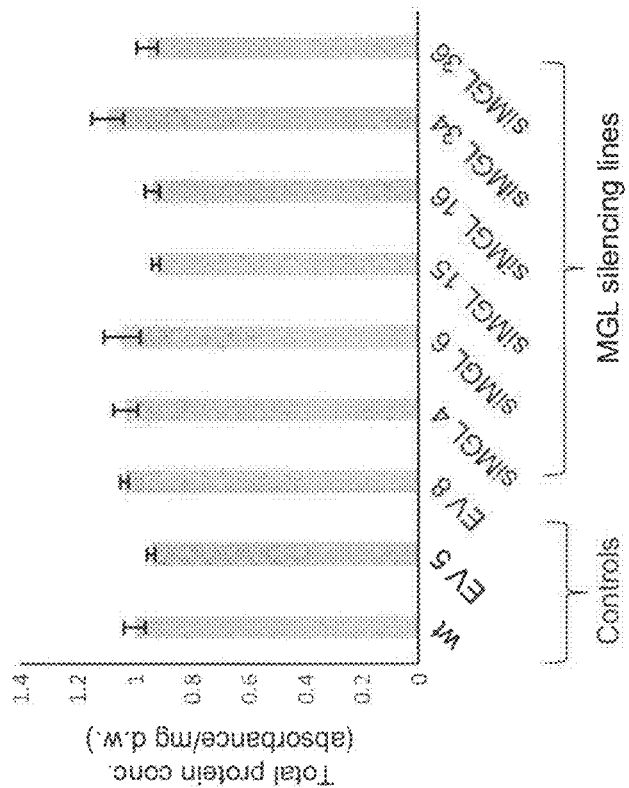
Figure 9A:
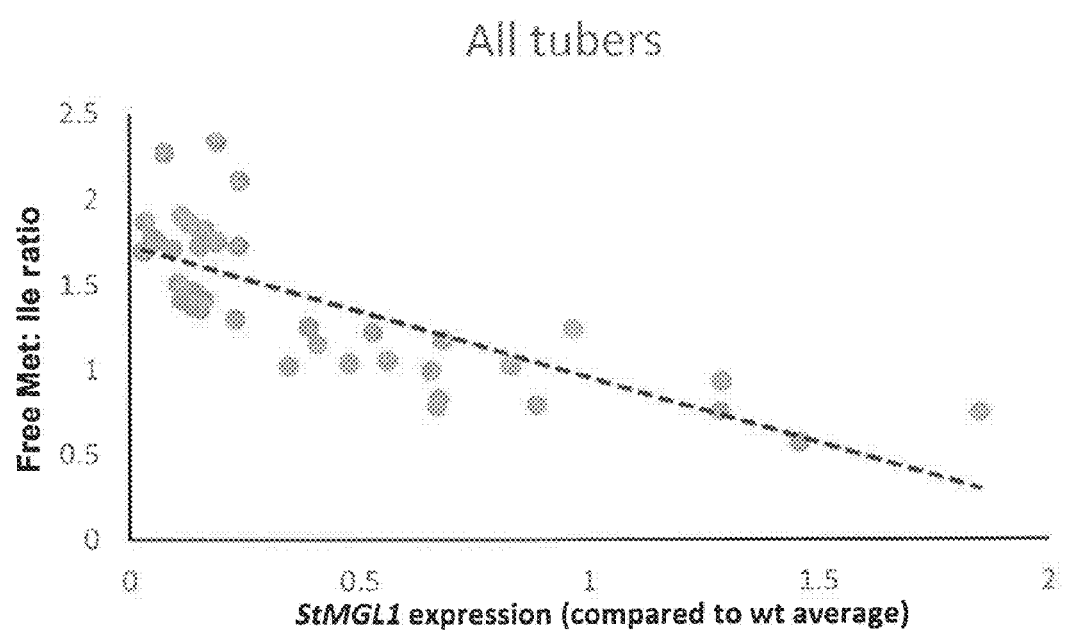
FIGS. 9a and 9b. Correlation of StMGL1 expression with free Met:Ile ratio.
Figure 9B:
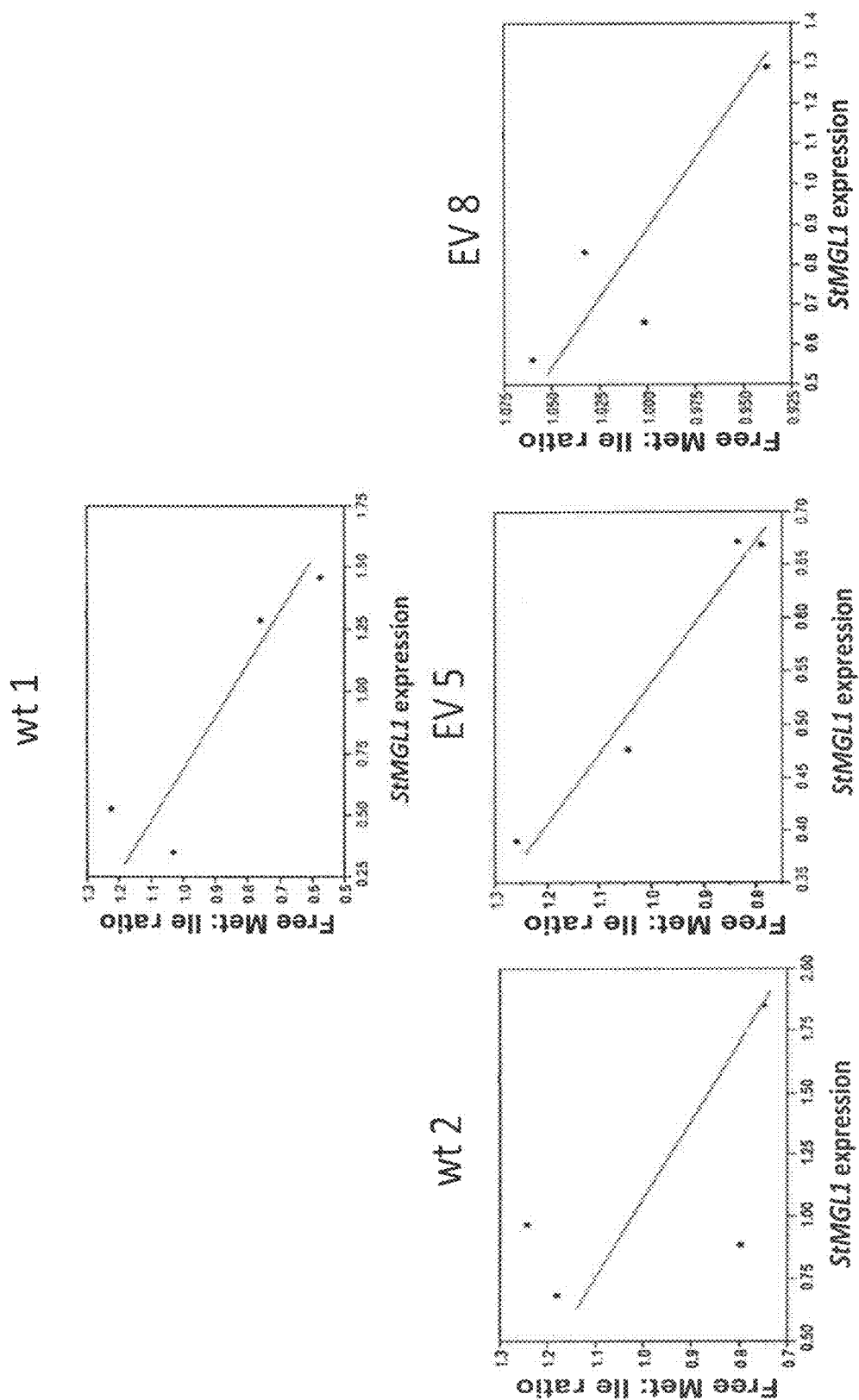

In *Arabidopsis*, MGL catalyzes the conversion of Met into methanethiol, ammonia, and 2-ketobutyrate, which is a precursor for Ile biosynthesis. Our hypothesis was that, if StMGL1 has the same function in potato, the Met to Ile ratio (Met:Ile) would be decreased in StMGL1-silenced plants due to reduced conversion of Met into Ile. Amino acid analysis of tuber samples verified this hypothesis, showing a doubling of the Met:Ile ration in all six StMGL1-silenced lines compared to the wild type controls. In contrast, the empty-vector transgenic plants had no difference in the Met:Ile ratio compared to wild type. Correlation analysis of StMGL1 expression and the ratio of Met:Ile on a tuber by tuber basis yield a significant negative linear regression, suggesting that the Met:Ile ratio in potato tubers is highly predictable based on the StMGL1 expression in the same tuber (FIG. 9A). This negative correlation also holds true in most cases when only tubers from the same plants are compared with one another (FIG. 9B). An interesting exception is siMGL 36, where the correlation is negative rather than positive. Would an increased Met:Ile ratio result in overall increased Met accumulation in these transgenic plants? Interestingly, although the abundance of Met as a proportion of all quantified amino acids was also significantly higher in most MGL-silenced plants (FIG. 8C), only two out of the six transgenic lines (siMGL 6 and siMGL 36) contained significantly higher soluble Met compared to wild type (FIG. 8D). As a large fraction of free Met is likely to be used for protein synthesis, we measured the levels of total protein in these tuber samples and found that there was no significant difference among all plant lines, suggesting that overall protein synthesis is not altered due to this metabolic change (FIG. 8E). When the total concentrations of 14 free amino acids were compared, the four transgenic lines that do not show increased free Met accumulation (siMGL 4, siMGL 15, siMGL 16, and siMGL 34) do have lower concentrations than wildtype controls, although this difference is not significant (P>0.05; FIG. 8F).

Figure 10B:
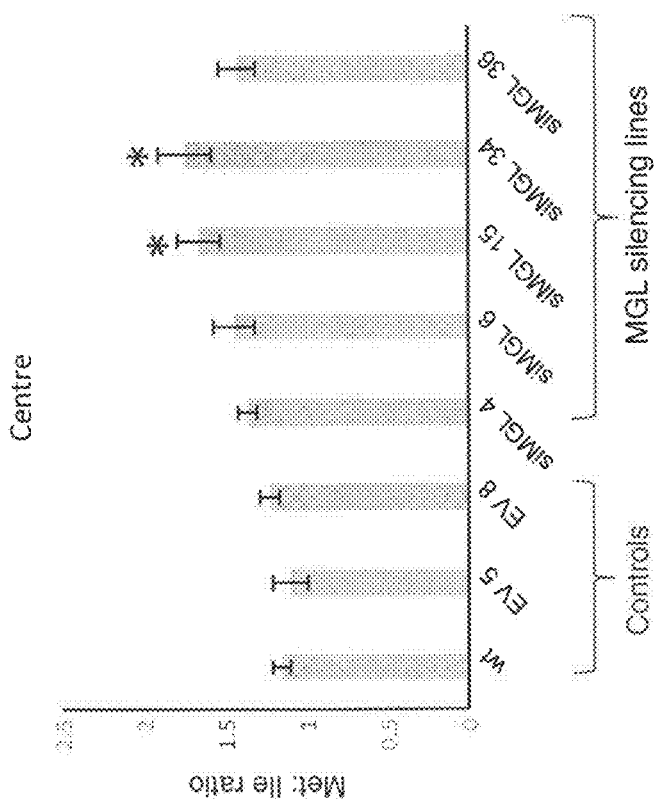
FIGS. 10a-10d. Amino acid phenotype of selected sample points from another planting cycle.
Figure 10A:
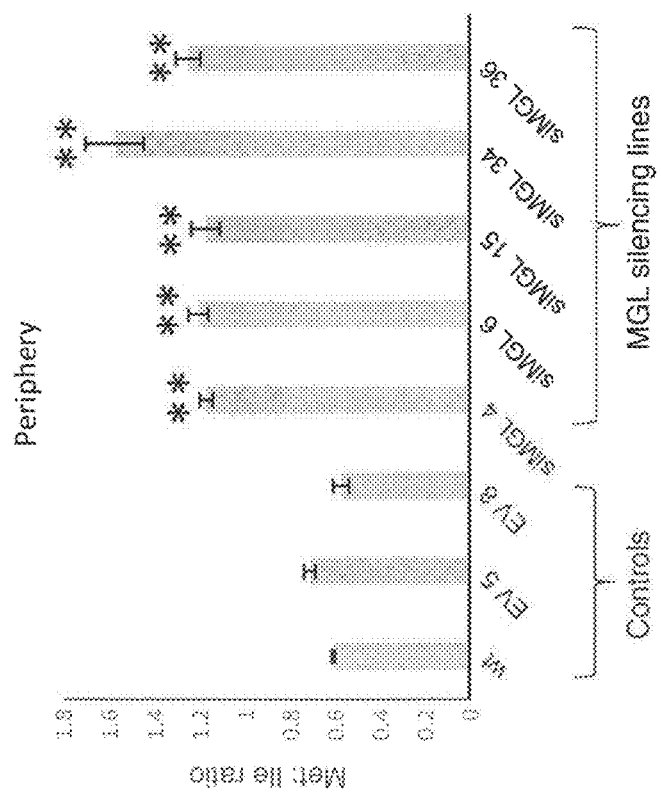
Figure 10D:
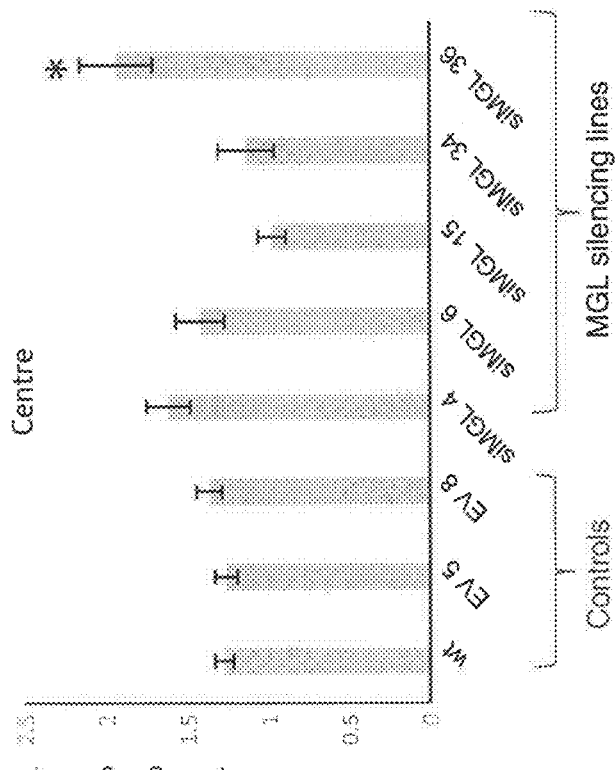
Figure 10C:
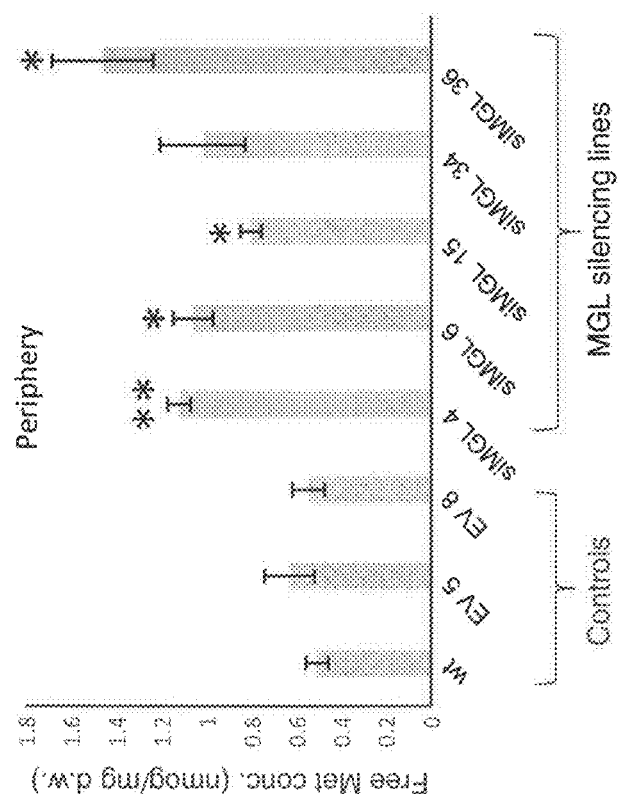

Previous potato amino acid studies have shown a considerable variation among different growing seasons. To determine whether or not the two transgenic lines siMGL 6 and siMGL 36 are just randomly showing higher Met in one particular planting season, we analyzed plant samples collected from another planting cycle that include all the same lines except siMGL 16, which was not available at that time. For each tuber, two sections were cut out, one from the tuber center, and another one from the periphery. Amino acid analysis of samples collected from the tuber periphery showed a significant increase of Met:Ile ratio in all siMLG lines (FIG. 10A), and increased soluble Met in all lines except siMGL 34 (FIG. 10C). Results obtained from the tuber centers were more variable, with many of them showing no significant differences compared to wild type (FIG. 10B, 10D).

Discussion

Some previous efforts to increase soluble Met in potato tubers by up-regulating biosynthesis did not produce the desired results, at least partly due to Met catabolism for Ile biosynthesis. To achieve higher Met accumulation, inhibition of catabolism should be considered along with increasing its biosynthesis. However, blocking the catabolism of amino acids can result in undesirable physiological effects if the downstream products are essential for healthy plant life. Among several Met catabolic enzymes, MGL may be the most suitable target for gene silencing because its product, 2-ketobutyrate, can also be synthesized from Thr by Thr deaminase. Previously, plant MGL activity has only been demonstrated in *Arabidopsis*, although there is some evidence for its function in other plant species. For example, it was proposed that MGL activity may explain concomitant Ile increases in rice plants overexpressing *Escherichia coli* serine acetyltransferase isoform (EcSAT), which resulted in significantly higher levels of soluble and protein-bound Met (Nguyen et al., 2012). Our study identifies a functional MGL in potato, an important crop species, and suggests a more universal role of MGL in plant Met catabolism.

Figure 9B:
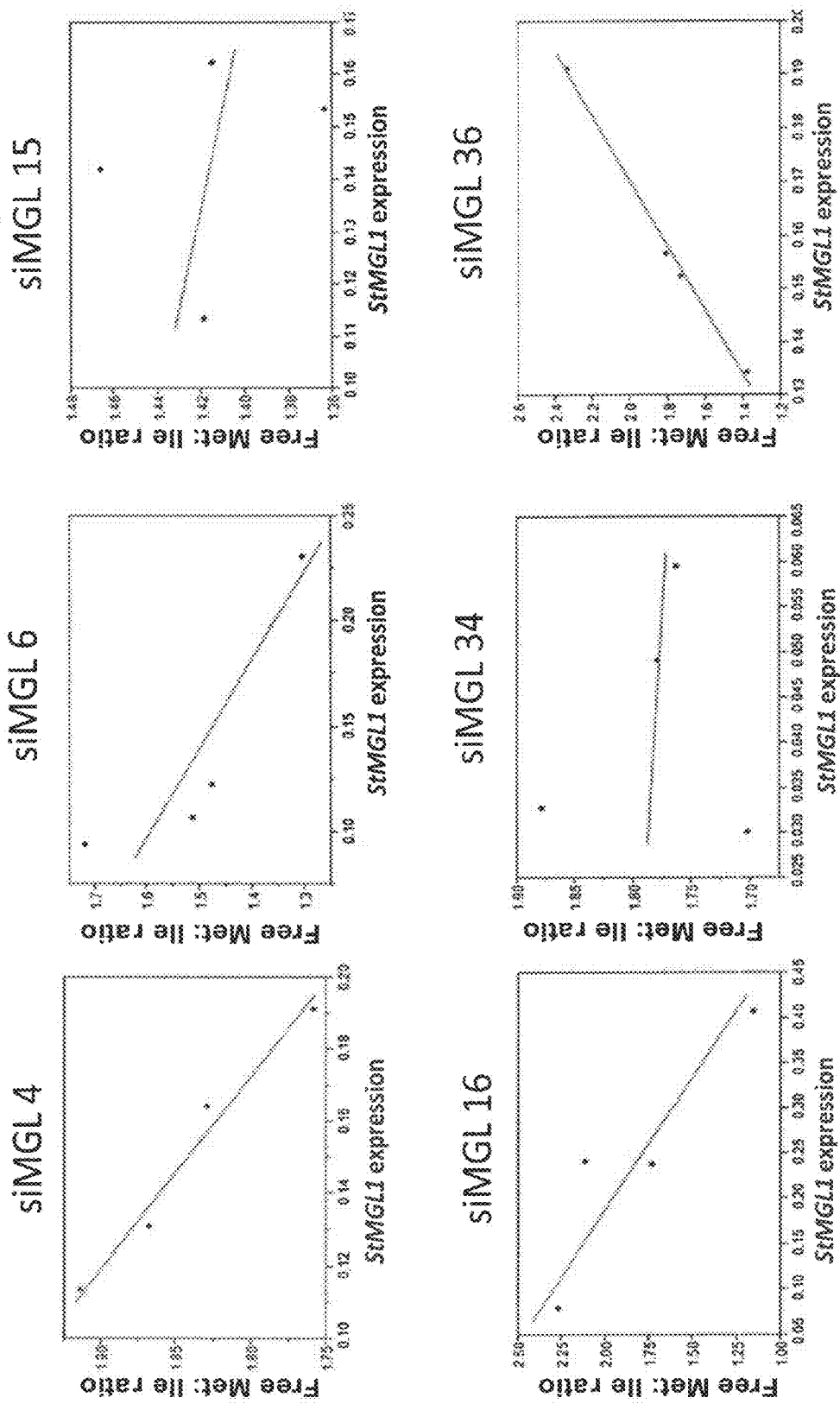

Unlike *Arabidopsis*, which has a diploid genome and can be studied as homozygous genetic material, Desiree and most other commercial potato varieties are heterozygous tetraploids. This complex genome structure makes it more difficult to study the functions of individual genes. The completion of the potato genome sequencing project, using a homozygous doubled-monoploid potato clone, set a milestone towards better understanding of the potato genome (Potato Genome Sequencing Consortium et al., 2011). We were able to identify two StMGL genes based on this genome assembly and annotation. RNAseq data and ESTs from publicly available databases suggest that StMGL1 is constitutively expressed in potatoes, whereas StMGL2 is expressed at a very low level (Potato Genome Sequencing Consortium et al., 2011). Our gene silencing results show a strong correlation between the decreased expression level of StMGL1 and the increased Met:Ile ratio in potato tubers, suggesting StMGL1 function is similar that of the *Arabidopsis* homolog, which catalyzes the catabolism of Met into methanethiol, 2-ketobutyrate, and ammonia, followed by biosynthesis of Ile from 2-ketobutyrate (Goyer et al., 2006; Joshi and Jander, 2009; Rébelllé et al., 2006). In the *Arabidopsis* mgl-2 mutant, an increased Met:Ile ratio was only observed in reproductive tissue. Future research will determine whether StMGL1 function is tissue-specific in potato. Since we did not use a tuber-specific promoter, the change in Met:Ile ratio in our transgenic plants could result from two possible mechanisms: (i) the amino acid profile is changed in the leaves, where most amino acid biosynthesis take place, and the altered ratio remains when amino acids were transported to tubers; and (ii) StMGL1 is active in potato tubers and controls the Met:Ile ratio more locally. Our results support the first mechanism, a functional role for StMGL1 in potato tubers, because the differences in the Met:Ile ratio of potato tubers from the same plant can be largely explained by the difference in StMGL1 expression in the tubers themselves (FIG. 9). Because all of the tubers on an individual plant share the same source of amino acid biosynthesis in the leaves, differences in tuber Met content are more likely caused by variation in the local MGL activity. Gene silencing by introduction of hairpin RNA, such as that used in this study, might not be absolutely specific to the target gene. In theory, off-target genes with very similar sequences could also be silenced. Considering that potato variety Desiree has a tetraploid genome, we cannot rule out that other StMGL1 homologs are also silenced by this approach. Yet this is also an advantage of RNAi silencing to tackle the problem of gene redundancy in polyploid genomes. Although the increased Met:Ile ratio is evident in all of our siMGL plants, the absolute concentration of soluble Met does not always increase. siMGL 36 has the highest free Met accumulation, but also has unhealthy-looking leaves and decreased tuber yield (FIG. 3). At this point, high Met could be either the cause or the result of these undesirable symptoms, but a similar observation was reported in a previous study to increase tuber Met (Zeh et al., 2001). Another line, siMGL 6, has a modest increase of Met compared to wildtype control, without any visible defects in growth and yield. The total Met content in four other siMGL lines is not significantly elevated, probably due to the slightly reduced total amino acid content. Positional effects of the randomly inserted transgenes are a likely cause for the observed phenotypic differences. We also note that this gene silencing strategy is more effective on the periphery, as StMGL1 silencing almost always results in higher soluble Met accumulation in the periphery, but not in the center of potato tubers (FIG. 10).

Free amino acid accumulation in plants is regulated through a combination of synthesis and catabolism (Karchi et al., 1994; Less and Galili, 2008). Thus, if Met catabolism limited overall tuber Met accumulation in previous studies (Kreft et al., 2003), combining such overexpression lines with MGL silencing might produce larger effects. Similarly, Increasing the activity of dihydrodipicolinate synthase, the rate-limiting step of lysine synthesis (Perl et al., 1992; Shaul and Galili, 1992), or decreasing catabolism by lysine ketoglutarate reductase (Stepansky et al., 2006; Tang et al., 1997), had only moderate effects on overall *Arabidopsis* lysine accumulation. However, a combination of the two approaches caused an 80-fold increase in *Arabidopsis* seed lysine content (Zhu and Galili, 2003). In translational research, lysine content in maize, where this is a limiting essential amino acid, has been increased in the same manner (Houmard et al., 2007; Huang et al., 2005; Reyes et al., 2009).

Another interesting observation from this study is the uneven three-dimensional distribution of free amino acids in potato tubers. Previous reports showed patterns of three-dimensional distribution of minerals in potato tubers, with most minerals being more abundant in the periphery. Distribution of free amino acids is opposite, with most free amino acids being enriched in the center. Two apparent exceptions are Glu and Asp, which fluctuate with different gradients depending on individual tubers (FIG. 7). Notably, Glu and Asp are also two of the major transport amino acids in plants and their dynamic distribution in potato tubers might reflect this unique attribute.

The amino acid distribution pattern not only offers new perspectives when designing experiments, but also has potential practical applications. For example, It has been proposed that making French fries as rings from the outside of the potato tubers, rather than as straight strips from the center, is a healthy alternative (Rommens et al., 2010). In particular, lower arginine content near the potato skin reduces formation of carcinogenic acrylamide via the Maillard reaction during frying (Rommens et al., 2010). However, since Met abundance is lower near the potato skin (FIG. 2), this suggests that there may also be disadvantages in terms of aroma and nutrient content when making French fry rings.

Metabolic pathways can be regulated in several ways, including through transcription, translation, post-translational modification, and allosteric feedback regulation. Our demonstration that Met to Ile conversion in potato tubers is highly negatively correlated with the local expression levels of StMGL1 not only validates the function of this enzyme in potato tubers, but also indicates that control of StMGL1 transcription is a critical regulator of this metabolic pathway. Silencing of StMGL1 using a construct expressed from the cauliflower mosaic virus 35S promoter does not always result in higher soluble Met. However, future research combining tuber-specific StMGL1 silencing to reduce Met catabolism with increased Met biosynthesis could yield potato plants with greatly elevated free Met.

REFERENCES

Amir R, Hacham Y and Galili G (2002) Cystathionine γ-synthase and threonine synthase operate in concert to regulate carbon flow towards methionine in plants. Trends in Plant Science 7:153-156.

Bartlem D, Lambein I, Okamoto T, Itaya A, Uda Y, Kijima F, Tamaki Y, Nambara E and Naito S (2000) Mutation in the Threonine Synthase Gene Results in an Over-Accumulation of Soluble Methionine in *Arabidopsis*. Plant Physiol 123:101-110.

Bombarely A, Menda N, Tecle I Y, Buels R M, Strickler S, Fischer-York T, Pujar A, Leto J, Gosselin J and Mueller L A (2011) The Sol Genomics Network (solgenomics.net): growing tomatoes using Perl. Nucleic Acids Res 39:D1149-D1155.

Bourgis F, Roje S, Nuccio M L, Fisher D B, Tarczynski M C, Li C J, Herschbach C, Rennenberg H, Pimenta M J, Shen T L, Gage D A and Hanson A D (1999) S-methylmethionine plays a major role in phloem sulfur transport and is synthesized by a novel type of methyltransferase. Plant Cell 11:1485-1497.

Chang S and Reddy B R (1971) Potato and potato chip flavor and aroma, (Research C ed).

Chiba Y, Ishikawa M, Kijima F, Tyson R H, Kim J, Yamamoto A, Nambara E, Leustek T, Wallsgrove R M and Naito S (1999) Evidence for autoregulation of cystathionine gamma-synthase mRNA stability in *Arabidopsis*. Science 286:1371.

Cohen S A and Michaud D P (1993) Synthesis of a fluorescent derivatizing reagent, 6-aminoquinolyl-N-hydroxy-succinimidyl carbamate, and its application for the analysis of hydrolysate amino acids via high-performance liquid chromatography. Analytical Biochemistry 211:279-287.

Curien G, Job D, Douce R and Dumas R (1998) Allosteric activation of *Arabidopsis* threonine synthase by S-adenosylmethionine. Biochemistry 37:13212-13221.

Dancs G, Kondrák M and Bánfalvi Z (2008) The effects of enhanced methionine synthesis on amino acid and anthocyanin content of potato tubers. BMC plant biology 8:65-65.

Di R, Kim J, Martin M N, Leustek T, Jhoo J, Ho C-T and Turner N E (2003) Enhancement of the primary flavor compound methional in potato by increasing the level of soluble methionine. JAgricFood Chem 51:5695-5702.

Goyer A, Collakova E, Shachar-Hill Y and Hanson A D (2006) Functional characterization of a methionine gamma-lyase in *Arabidopsis* and its implication in an alternative to the reverse trans-sulfuration pathway. Plant and Cell Physiology 48:232-242.

Helliwell C (2003) Constructs and methods for high-throughput gene silencing in plants. Methods 30:289-295.

Hesse H, Kreft O, Maimann S, Zeh M and Hoefgen R (2004) Current understanding of the regulation of methionine biosynthesis in plants. Journal of Experimental Botany 55:1799-1808.

Houmard N M, Mainville J L, Bonin C P, Huang S, Luethy M H and Malvar T M (2007) High-lysine corn generated by endosperm-specific suppression of lysine catabolism using RNAi. Plant Biotechnol J5:605-614.

Hoza B, Murray-Close D, Arnold L E, Hinshaw S P and Hechtman L (2010) Time-dependent changes in positively biased self-perceptions of children with attention-deficit/hyperactivity disorder: a developmental psychopathology perspective. Dev Psychopathol 22:375-390.

Huang S, Kruger D E, Frizzi A, D'Ordine R L, Florida C A, Adams W R, Brown W E and Luethy M H (2005) High-lysine corn produced by the combination of enhanced lysine biosynthesis and reduced zein accumulation. Plant Biotechnol J 3:555-569.

Jander G and Joshi V (2010) Recent progress in deciphering the biosynthesis of aspartate-derived amino acids in plants. Mol Plant 3:54-65.

Joshi V and Jander G (2009) *Arabidopsis* methionine gamma-lyase is regulated according to isoleucine biosynthesis needs but plays a subordinate role to threonine deaminase. *Plant Physiol* 151:367-378.

Karchi H, Shaul 0 and Galili G (1994) Lysine synthesis and catabolism are coordinately regulated during tobacco seed development. *Proc Natl Acad Sci USA* 91:2577-2581.

Kim J, Lee M, Chalam R, Martin M N, Leustek T and Boerjan W (2002) Constitutive overexpression of cystathionine γ-synthase in *Arabidopsis* leads to accumulation of soluble methionine and S-methylmethionine. *Plant Physiol* 128:95-107.

Koch W, Kwart M, Laubner M, Heineke D, Stransky H, Frommer W B and Tegeder M (2003) Reduced amino acid content in transgenic potato tubers due to antisense inhibition of the leaf H+/amino acid symporter StAAP1. *Plant J* 33:211-220.

Kreft O, Hoefgen R and Hesse H (2003) Functional analysis of cystathionine γ-synthase in genetically engineered potato plants. *Plant Physiol* 131:1843-1854.

Kumar G N M, Iyer S and Knowles N R (2007) Extraction of RNA from fresh, frozen, and lyophilized tuber and root tissues. *JAgricFood Chem* 55:1674-1678.

Less H and Galili G (2008) Principal transcriptional programs regulating plant amino acid metabolism in response to abiotic stresses. *Plant Physiol* 147:316-330.

Lindsay R C (1996) Flavors, in Food chemistry (Fennema OR ed), New York: Marcel Dekker.

Mourad G and King J (1995) L-O-methylthreonine-resistant mutant of *Arabidopsis* defective in isoleucine feedback regulation. *Plant Physiol* 107:43-52.

Nguyen H C, Hoefgen R and Hesse H (2012) Improving the nutritive value of rice seeds: elevation of cysteine and methionine contents in rice plants by ectopic expression of a bacterial serine acetyltransferase. *Journal of Experimental Botany* 63:5991-6001.

Nicot N (2005) Housekeeping gene selection for real-time RT-PCR normalization in potato during biotic and abiotic stress. *Journal of Experimental Botany* 56:2907-2914.

Onouchi H, Nagami Y, Haraguchi Y, Nakamoto M, Nishimura Y, Sakurai R, Nagao N, Kawasaki D, Kadokura Y and Naito S (2005) Nascent peptide-mediated translation elongation arrest coupled with mRNA degradation in the CGS1 gene of *Arabidopsis*. *Genes Dev* 19:1799.

Perl A, Shaul O and Galili G (1992) Regulation of lysine synthesis in transgenic potato plants expressing a bacterial dihydrodipicolinate synthase in their chloroplasts. *Plant Mol Biol* 19:815-823.

Potato Genome Sequencing Consortium, Xu X, Pan S, Cheng S, Zhang B, Mu D, Ni P, Zhang G, Yang S, Li R, Wang J, Orjeda G, Guzman F, Torres M, Lozano R, Ponce O, Martinez D, De la Cruz G, Chakrabarti S K, Patil V U, Skryabin K G, Kuznetsov B, Ravin N V, Kolganova T V, Beletsky A V, Mardanov A V, Di Genova A, Bolser D M, Martin D M, Li G, Yang Y, Kuang H, Hu Q, Xiong X, Bishop G J, Sagredo B, Mejia N, Zagorski W, Gromadka R, Gawor J, Szczesny P, Huang S, Zhang Z, Liang C, He J, Li Y, He Y, Xu J, Zhang Y, Xie B, Du Y, Qu D, Bonierbale M, Ghislain M, Herrera Mdel R, Giuliano G, Pietrella M, Perrotta G, Facella P, O'Brien K, Feingold S E, Barreiro L E, Massa G A, Diambra L, Whitty B R, Vaillancourt B, Lin H, Massa A N, Geoffroy M, Lundback S, DellaPenna D, Buell C R, Sharma S K, Marshall D F, Waugh R, Bryan G J, Destefanis M, Nagy I, Milbourne D, Thomson S J, Fiers M, Jacobs J M, Nielsen K L, Sonderkaer M, Iovene M, Torres G A, Jiang J, Veilleux R E, Bachem C W, de Boer J, Borm T, Kloosterman B, van Eck H, Datema E, Hekkert B, Goverse A, van Ham R C and Visser R G (2011) Genome sequence and analysis of the tuber crop potato. *Nature* 475:189-195.

Rébeillé F, Jabrin S, Bligny R, Loizeau K, Gambonnet B, Wilder V V, Douce R and Ravanel S (2006) Methionine catabolism in *Arabidopsis* cells is initiated by a γ-cleavage process and leads to S-methylcysteine and isoleucine syntheses. *Proceedings of the National Academy of Sciences* 103:15687-15692.

Reyes A R, Bonin C P, Houmard N M, Huang S and Malvar T M (2009) Genetic manipulation of lysine catabolism in maize kernels. *Plant Mol Biol* 69:81-89.

Rinder J, Casazza A P, Hoefgen R and Hesse H (2008) Regulation of aspartate-derived amino acid homeostasis in potato plants (*Solanum tuberosum* L.) by expression of *E. coli* homoserine kinase. *Amino Acids* 34:213-222.

Rommens C M, Shakya R, Heap M and Fessenden K (2010) Tastier and healthier alternatives to French fries. *J Food Sci* 75:H109-H115.

Shaul O and Galili G (1992) Increased lysine synthesis in transgenic tobacco plants expressing a bacterial dihydrodipicolinate synthase in their chloroplasts. *Plant J* 2:203-209.

Shen B, Li C and Tarczynski M C (2002) High free-methionine and decreased lignin content result from a mutation in the *Arabidopsis* S-adenosyl-L-methionine synthetase 3 gene. *Plant J* 29:371-380.

Stepansky A, Less H, Angelovici R, Aharon R, Zhu X and Galili G (2006) Lysine catabolism, an effective versatile regulator of lysine level in plants. *Amino Acids* 30:121-125.

Tang G, Miron D, Zhu-Shimoni J X and Galili G (1997) Regulation of lysine catabolism through lysine-ketoglutarate reductase and saccharopine dehydrogenase in *Arabidopsis*. *Plant Cell* 9:1305-1316.

Van Eck J, Conlin B, Garvin D F, Mason H, Navarre D A and Brown C R (2007) Enhancing beta-carotene content in potato by rnai-mediated silencing of the beta-carotene hydroxylase gene. *American Journal of Potato Research* 84:331-342.

Wesley S V, Helliwell C A, Smith N A, Wang M, Rouse D T, Liu Q, Gooding P S, Singh S P, Abbott D, Stoutjesdijk P A, Robinson S P, Gleave A P, Green A G and Waterhouse P M (2001) Construct design for efficient, effective and high-throughput gene silencing in plants. *The Plant Journal* 27:581-590.

Woolfe J A, Poats S V and International Potato C (1987) *The potato in the human diet*. Cambridge; New York:Cambridge University Press.

Zeh M, Casazza A P, Kreft O, Roessner U, Bieberich K, Willmitzer L, Hoefgen R and Hesse H (2001) Antisense inhibition of threonine synthase leads to high methionine content in transgenic potato plants. *Plant Physiol* 127:792-802.

Zhu X and Galili G (2003) Increased lysine synthesis coupled with a knockout of its catabolism synergistically boosts lysine content and also transregulates the metabolism of other amino acids in *Arabidopsis* seeds. *Plant Cell* 15:845-853.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A vector comprising an RNAi effective to down modulate expression of methionine gamma lyase in a target plant, thereby increasing methionine content in plant cells expressing said RNAi, wherein said RNAi is SEQ ID NO: 1.

2. The vector comprising the RNAi of claim 1 wherein said RNAi is operably linked to at least one regulatory sequence.

3. A method for producing a potato plant having increased methionine content in tubers comprising
   a) transforming a potato plant cell with the RNAi of claim 1, and regenerating a plant from the transformed plant cell.

4. A method for transforming a cell comprising transforming a cell with the RNAi of claim 1.

5. A potato plant cell comprising the RNAi of claim 1.

6. A potato plant produced from the transformed potato plant cell of claim 3.

7. A seed comprising the RNAi of claim 1.

8. A method for increasing methionine content in potatoes comprising:
   (a) transforming potato plant cells with the RNAi of claim 1;
   (b) growing fertile mature plants from the transformed plant cells obtained from step (a) under conditions suitable to obtain potatoes; and
   (c) harvesting potatoes containing increased levels of methionine compared to potatoes obtained from plants lacking said RNAi.

* * * * *